(12) United States Patent
Kondo

(10) Patent No.: US 9,218,802 B2
(45) Date of Patent: Dec. 22, 2015

(54) ULTRASONIC PROBE AND ULTRASONIC DIAGNOSTIC APPARATUS

(75) Inventor: Yuji Kondo, Kaisei-machi (JP)

(73) Assignee: FUJIFILM CORPORATION, Tokyo (JP)

( * ) Notice: Subject to any disclaimer, the term of this patent is extended or adjusted under 35 U.S.C. 154(b) by 644 days.

(21) Appl. No.: 12/591,201

(22) Filed: Nov. 12, 2009

(65) Prior Publication Data

US 2010/0121194 A1    May 13, 2010

(30) Foreign Application Priority Data

Nov. 13, 2008  (JP) ................. 2008-290894
Mar. 13, 2009  (JP) ................. 2009-061086

(51) Int. Cl.
| | |
|---|---|
| G10K 11/34 | (2006.01) |
| A61B 8/00 | (2006.01) |
| G01S 7/52 | (2006.01) |
| G01S 7/00 | (2006.01) |

(52) U.S. Cl.
CPC .............. *G10K 11/346* (2013.01); *A61B 8/00* (2013.01); *A61B 8/565* (2013.01); *G01S 7/5208* (2013.01); *G01S 7/52028* (2013.01); *A61B 8/4472* (2013.01); *G01S 7/003* (2013.01)

(58) Field of Classification Search
CPC ........ A61B 8/00; A61B 8/4472; A61B 8/565; G01S 7/003; G01S 7/52028
USPC ....................................... 600/459
See application file for complete search history.

(56) References Cited

U.S. PATENT DOCUMENTS

| | | | | | |
|---|---|---|---|---|---|
| 4,835,689 | A | * | 5/1989 | O'Donnell | 250/580 |
| 6,520,915 | B1 | * | 2/2003 | Lin et al. | 600/453 |
| 2007/0236374 | A1 | | 10/2007 | Brueske et al. | |
| 2008/0114249 | A1 | | 5/2008 | Randall et al. | |

FOREIGN PATENT DOCUMENTS

| | | |
|---|---|---|
| EP | 1860461 | 11/2007 |
| JP | S61-191345 A | 8/1986 |
| JP | 03-136638 A | 6/1991 |

(Continued)

OTHER PUBLICATIONS

Notification of Reasons for Rejection issued by JPO on Sep. 3, 2013, in connection with corresonding Japanese Patent Application No. 2008-290894.

*Primary Examiner* — James Kish
*Assistant Examiner* — Saurel J Selkin
(74) *Attorney, Agent, or Firm* — Jean C. Edwards, Esq.; Edwards Neils PLLC

(57) ABSTRACT

The number of signal lines connecting an ultrasonic probe and an ultrasonic diagnostic apparatus main body is reduced or wireless communication is realized by reducing a volume of data of reception signals outputted from plural ultrasonic transducers. The ultrasonic probe includes: plural ultrasonic transducers for transmitting ultrasonic waves according to drive signals and receiving ultrasonic echoes to output reception signals; signal processing units for performing orthogonal detection processing or orthogonal sampling processing on the reception signals to generate two signals representing a complex baseband signal; sampling units for sampling the two signals to generate parallel sample data; a serializing unit for converting the parallel sample data into serial sample data; and a transmitting unit for transmitting the serial sample data.

10 Claims, 15 Drawing Sheets

(56) References Cited

FOREIGN PATENT DOCUMENTS

| JP | 06-335481 A | 12/1994 |
| JP | 11-299776 A | 11/1999 |
| JP | 2003-299648 | 10/2003 |
| JP | 2004-350962 A | 12/2004 |
| JP | 2008-018107 | 1/2008 |
| JP | 2008-113793 A | 5/2008 |

* cited by examiner

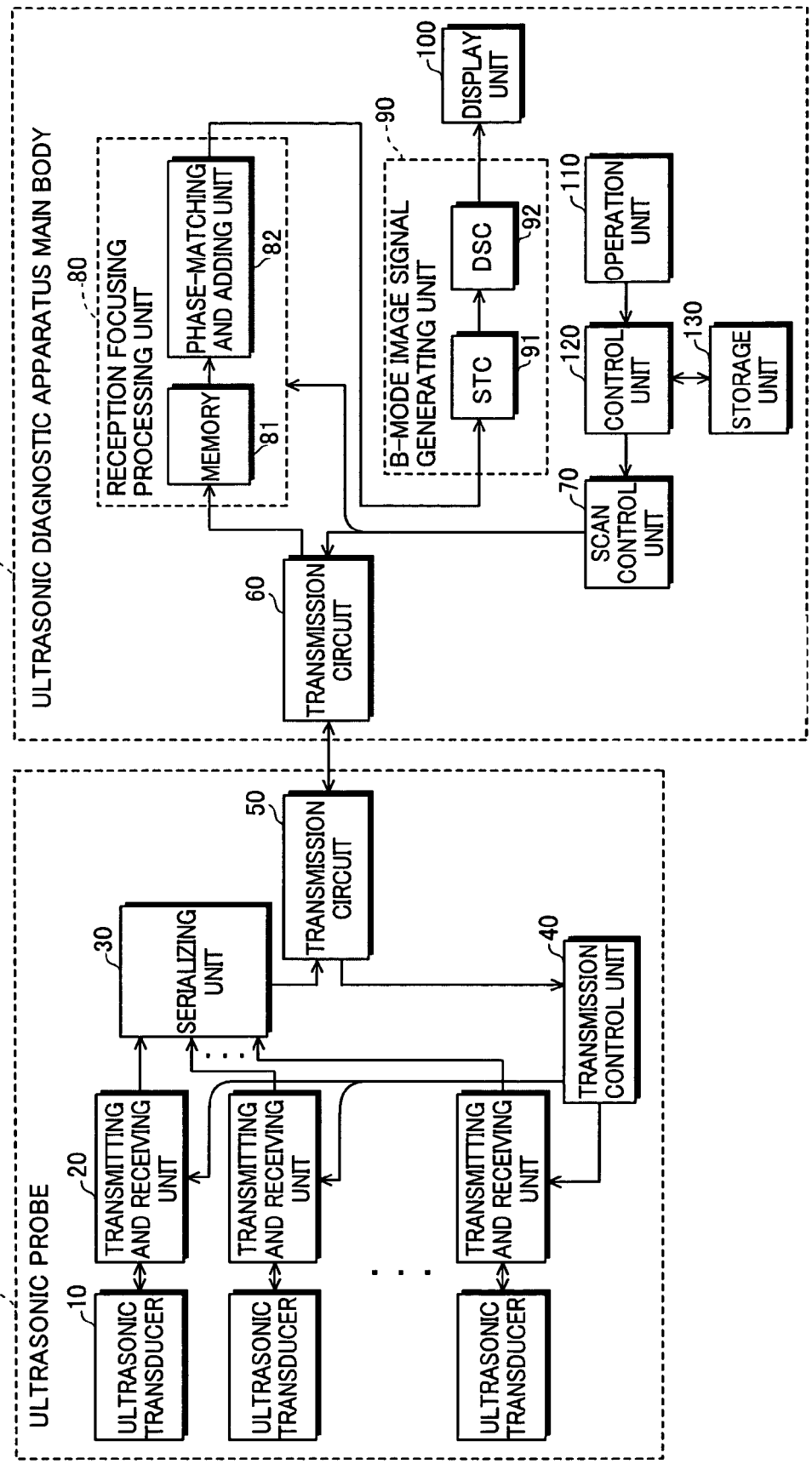

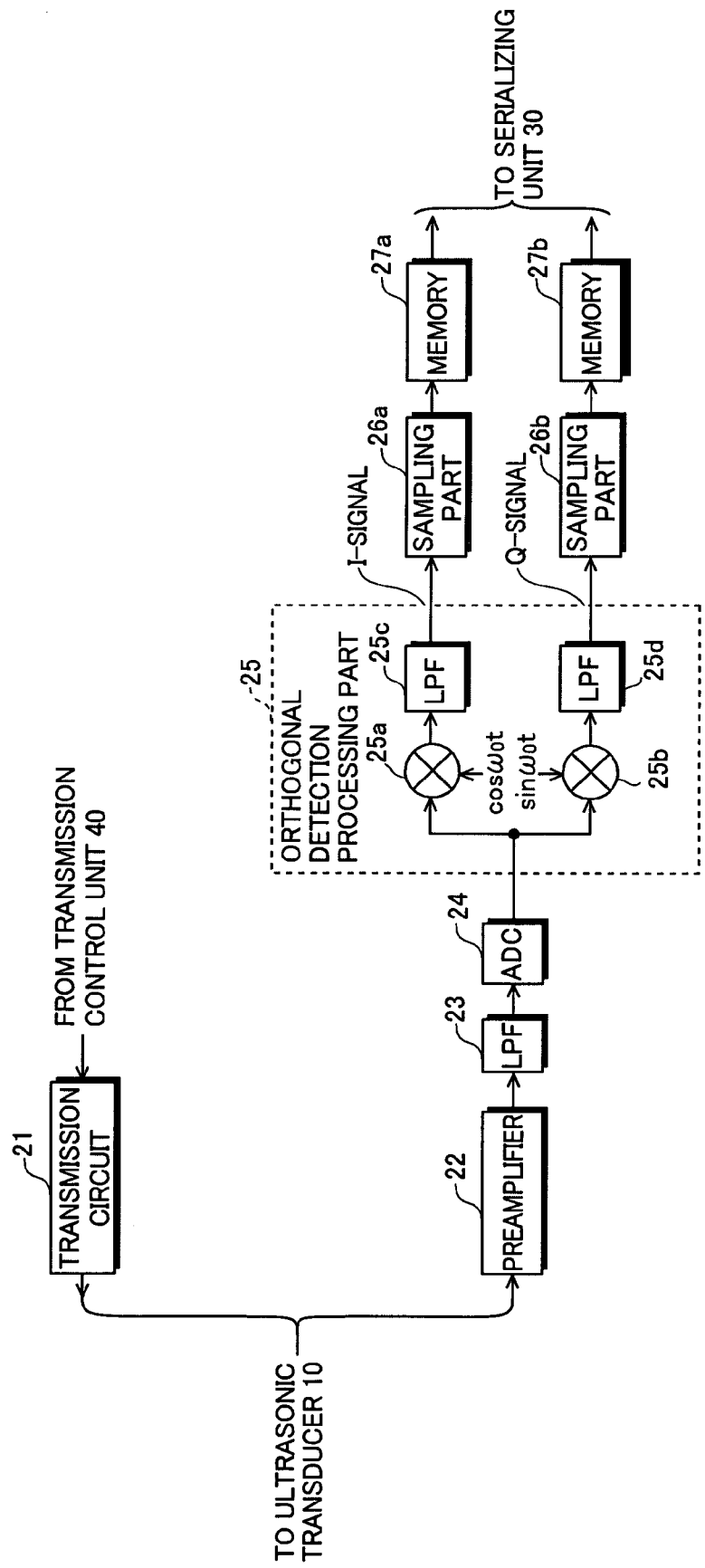

ULTRASONIC PROBE AND ULTRASONIC DIAGNOSTIC APPARATUS

CROSS-REFERENCE TO RELATED APPLICATION

The present application claims priority from Japanese Patent Applications No. 2008-290894 filed on Nov. 13, 2008 and No. 2009-061086 filed on Mar. 13, 2009, the contents of which are incorporated herein by reference in their entirety.

BACKGROUND OF THE INVENTION

1. Field of the Invention

The present invention relates to an ultrasonic probe including plural ultrasonic transducers for transmitting and receiving ultrasonic waves, and an ultrasonic diagnostic apparatus for generating ultrasonic diagnostic images by using the ultrasonic probe.

2. Description of a Related Art

In medical fields, various imaging technologies have been developed for observation and diagnoses within an object to be inspected. Especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in obstetrics, but also gynecology, circulatory system, digestive system, and so on.

The principle of ultrasonic imaging is as follows. Ultrasonic waves are reflected at a boundary between regions having different acoustic impedances like a boundary between structures within the object. Therefore, by transmitting ultrasonic beams into the object such as a human body, receiving ultrasonic echoes generated within the object, and obtaining reflection points where the ultrasonic echoes are generated or reflection intensity, outlines of structures (e.g., internal organs, diseased tissues, and so on) existing within the object can be extracted.

Generally, in an ultrasonic diagnostic apparatus, an ultrasonic probe including plural ultrasonic transducers (vibrators) having transmitting and receiving functions of ultrasonic waves is used. Reception signals outputted from the vibrators, which have received ultrasonic echoes, have delays according to differences of distances from the focal point of ultrasonic waves to the respective vibrators. Accordingly, beam forming processing (reception focusing processing) for forming a focal point in a specific position is performed by providing the delays according to the positions of the vibrators to those reception signals and then adding those reception signals to one another. In this regard, until the reception signals are added to one another, those reception signals are handled as parallel data.

The reception focusing processing is typically performed by digital signal processing. That is, the A/D-converted reception signals are accumulated in a memory, and then, read out while the readout times are changed as needed, moderately interpolation-processed, and added to one another. When the reception signals are added to one another, the number of signal channels becomes one, and therefore, signal transmission can be performed by wireless communication. Accordingly, if a circuit for performing reception focusing processing is incorporated in the ultrasonic probe, a number of signal lines connecting the ultrasonic probe with the ultrasonic diagnostic apparatus main body can be reduced, or wireless communication can be realized.

However, in the reception focusing processing, the amounts of delay provided to the reception signals are different depending on the position of the focal point, and therefore, the control of the readout times from the memory becomes extremely complex, and a large-scale circuit is necessary. If such a circuit is incorporated into the ultrasonic probe, the probe becomes too large in size for practical use to be easily operated with one hand.

As a related technology, Japanese Patent Application Publication JP-P2003-299648A discloses an ultrasonic diagnostic apparatus having an ultrasonic probe that can maintain and improve operability because a thinner and lighter transmission cable can be realized even when a number of vibrating elements is increased with higher definition. The ultrasonic diagnostic apparatus includes an ultrasonic probe for transmitting and receiving ultrasonic pulses to and from a living body by using plural vibrating elements, and an apparatus main body connected to the ultrasonic probe via a transmission cable, for generating transmission signals for transmitting ultrasonic pulses from the ultrasonic probe and forming an ultrasonic image from reception signals based on ultrasonic pulses (echoes) reflected by the living body and received by the ultrasonic probe. The ultrasonic diagnostic apparatus is characterized in that the transmission signals and the reception signals passed between the ultrasonic probe and the apparatus main body via the transmission cable are time-divisionally segmented corresponding to the respective vibrating elements and chipped before transmission and the respective chips are sequentially transmitted by using a common signal line within the transmission cable.

However, in the ultrasonic diagnostic apparatus of JP-P2003-299648A, since the reception signals outputted from the respective vibrating elements are transmitted in an unchanged band, the volume of data cannot be reduced and a high transmission rate is necessary. Further, since the reception signals are time-divisionally transmitted, there is no guarantee that the beam forming processing can reliably be performed after transmission.

Further, Japanese Patent Application Publication JP-P2008-18107A discloses a wireless ultrasonic diagnostic apparatus for wireless transmission between an ultrasonic probe and an apparatus main body. In the ultrasonic diagnostic apparatus, the ultrasonic probe includes plural vibrators, amplifiers and A/D (analog/digital) converters corresponding to those vibrators, a digital beamformer, a PS (parallel/serial) converting unit, a control data inserting unit, a modulator, and a power amplifier. The digital beam forming processing is performed within the ultrasonic probe to generate phase-matched and added data, and further, the phase-matched and added data is parallel/serial-converted.

However, in order to perform digital beam forming processing within the ultrasonic probe, a front-end circuit in a conventional ultrasonic diagnostic apparatus as a whole should be accommodated within the ultrasonic probe, and the circuit size becomes enormous.

SUMMARY OF THE INVENTION

The present invention has been achieved in view of the above-mentioned points. A purpose of the present invention is to reduce the number of signal lines connecting an ultrasonic probe and an ultrasonic diagnostic apparatus main body or realize wireless communication by reducing a volume of data of reception signals outputted from plural ultrasonic transducers.

In order to accomplish the above-mentioned purpose, an ultrasonic probe according to one aspect of the present invention includes: plural ultrasonic transducers for transmitting ultrasonic waves according to drive signals and receiving ultrasonic echoes to output reception signals; signal processing means for performing orthogonal detection processing or orthogonal sampling processing on the reception signal outputted from each ultrasonic transducer to generate two signals representing a complex baseband signal; sampling means for sampling the two signals generated by the signal processing means to generate parallel sample data; serializing means for converting the parallel sample data generated by the sampling means into serial sample data; and transmitting means for transmitting the serial sample data converted by the serializing means.

According to the one aspect of the present invention, the ultrasonic probe performs orthogonal detection processing or orthogonal sampling processing on a reception signal outputted from each ultrasonic transducer to generate two signals representing a complex baseband signal, and converts parallel sample data generated by sampling the two signals into serial sample data to transmit it to the ultrasonic diagnostic apparatus main body, and thereby, the number of signal lines connecting the ultrasonic probe and the ultrasonic diagnostic apparatus main body can be reduced or wireless communication can be realized by reducing a volume of data of reception signals outputted from plural ultrasonic transducers.

BRIEF DESCRIPTION OF THE DRAWINGS

FIG. 1 is a block diagram showing a configuration of an ultrasonic diagnostic apparatus according to the first embodiment of the present invention;

FIG. 2 shows a first configuration example of a transmitting and receiving unit as shown in FIG. 1;

DESCRIPTION OF THE PREFERRED EMBODIMENTS

Figure 3A:
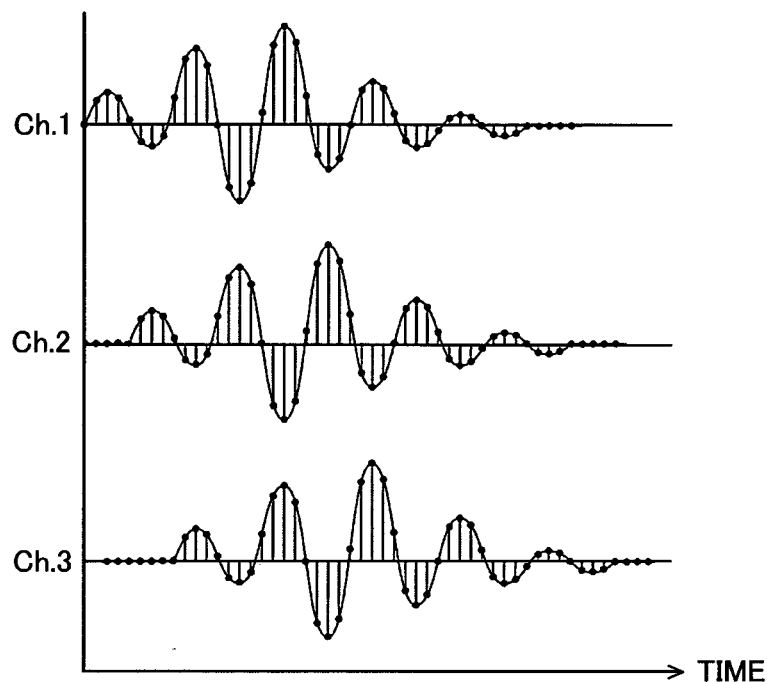
FIG. 3A is a waveform chart showing sampling by an ADC as shown in FIG. 2.

Hereinafter, embodiments of the present invention will be explained in detail with reference to the drawings. The same reference characters are assigned to the same component elements and the explanation thereof will be omitted.

FIG. 1 is a block diagram showing a configuration of an ultrasonic diagnostic apparatus according to the first embodiment of the present invention. As shown in FIG. 1, the ultrasonic diagnostic apparatus includes an ultrasonic probe 1 according to the first embodiment of the present invention and an ultrasonic diagnostic apparatus main body 2.

The ultrasonic probe 1 may be an external probe of linear-scan type, convex-scan type, sector-scan type, or the like, or an ultrasonic endoscopic probe of radial-scan type or the like. As shown in FIG. 1, the ultrasonic probe 1 includes plural ultrasonic transducers 10 forming a one-dimensional or two-dimensional transducer array, plural channels of transmitting and receiving units 20, a serializing unit 30, a transmission control unit 40, and a transmission circuit 50.

The plural ultrasonic transducers 10 transmit ultrasonic waves according to applied drive signals and receive propagating ultrasonic echoes to output reception signals. Each ultrasonic transducer includes a vibrator having electrodes formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like.

When a pulsed or continuous wave voltage is applied to the electrodes of the vibrator, the piezoelectric material expands and contracts. By the expansion and contraction, pulse or continuous ultrasonic waves are generated from the respective vibrators, and an ultrasonic beam is formed by synthesizing these ultrasonic waves. Further, the respective vibrators expand and contract by receiving the propagating ultrasonic waves to generate electric signals. These electric signals are outputted as reception signals of ultrasonic waves.

Each channel of transmitting and receiving unit 20 generates a drive signal under the control of the transmission control unit 40 and supplies the drive signal to the ultrasonic transducer 10, performs orthogonal detection processing or the like on reception signal outputted from the ultrasonic transducer 10 to generate a complex baseband signal (I-signal and Q-signal), and supplies parallel sample data generated by sampling the I-signal and the Q-signal to the serializing unit 30.

FIG. 2 shows a first configuration example of the transmitting and receiving unit as shown in FIG. 1. As shown in FIG. 2, each channel of transmitting and receiving unit 20 includes a transmission circuit 21, a preamplifier 22, a lowpass filter (LPF) 23, an analog/digital converter (ADC) 24, an orthogonal detection processing part 25, sampling parts 26a and 26b, and memories 27a and 27b. Here, the transmission circuit 21 to the orthogonal detection processing part 25 form signal processing means.

The transmission circuit 21 includes a pulser, for example, and generates a drive signal under the control of the transmission control unit 40, and supplies the generated drive signal to the ultrasonic transducer 10. The transmission control unit 40 as shown in FIG. 1 controls the operation of the plural channels of transmission circuits 21 according to a scan control signal outputted from the transmission circuit 50. For example, the transmission control unit 40 selects one transmission delay pattern from among plural transmission delay patterns according to a transmission direction set by the scan control signal, and sets delay times to be provided to the drive signals for the plural ultrasonic transducers 10 based on the selected transmission delay pattern. Alternatively, the transmission control unit 40 may set delay times such that the ultrasonic waves transmitted at a time from the plural ultrasonic transducers 10 reach the entire imaging region of the object.

The plural channels of transmission circuits 21 adjust amounts of delay of the drive signals and supply the drive signals to the plural ultrasonic transducers 10 such that the ultrasonic waves transmitted from the plural ultrasonic transducers 10 form an ultrasonic beam, or supply drive signals to the plural ultrasonic transducers 10 such that the ultrasonic waves transmitted at a time from the plural ultrasonic transducers 10 reach the entire imaging region of the object, according to the transmission delay pattern selected by the transmission control unit 40.

The preamplifier 22 amplifies the reception signal (RF signal) outputted from the ultrasonic transducer 10, and the LPF 23 limits a band of the reception signal outputted from the preamplifier 21 to prevent aliasing in A/D conversion. The ADC 24 converts the analog reception signal outputted from the LPF 23 into a digital reception signal. For example, if the frequency of ultrasonic waves is about 5 MHz, a sampling frequency of 40 MHz is used. In this case, a distance within the living body corresponding to one sample is about 0.038 mm, and data to the depth of about 15.7 cm is obtained from 4096 samples.

Assuming that the number of ultrasonic transducers in the reception aperture is 64 and that 100 ultrasonic reception lines (sound rays) with respect to one frame of ultrasonic diagnostic image are necessary, the volume of data necessary for display of one frame of image is $4096 \times 64 \times 100 \approx 26 \times 10^6$, and data transfer of about $260 \times 10^6$/sec is necessary for display of ten frames per second. Here, resolving power necessary for the ultrasonic diagnostic image is typically about 12 bits for one datum, and therefore, a transmission bit rate of about 3120 Mbps is necessary to transmit the above-mentioned data.

In this way, if data is serialized while it remains as the RF signal, the transmission bit rate becomes extremely higher and the communication speed or the operation speed of the memories cannot keep up with the transmission bit rate. On the other hand, as described in the description of a related art, if the data is serialized after reception focusing processing, the transmission bit rate can be reduced. However, a circuit for reception focusing processing is large-scaled and hard to be incorporated into the ultrasonic probe. Accordingly, in the embodiment, orthogonal detection processing or the like is performed on the reception signal to drop the frequency range of the reception signal to the baseband frequency range and then the data is serialized, and thereby, the transmission bit rate is reduced.

The orthogonal detection processing part 25 performs orthogonal detection processing on the reception signal to generate a complex baseband signal (I-signal and Q-signal). As shown in FIG. 2, the orthogonal detection processing part 25 includes mixers (multiplication circuits) 25a and 25b, and lowpass filters (LPFs) 25c and 25d. The mixer 25a multiplies the reception signal, that has been converted into the digital signal by the ADC 24, by a local oscillation signal $\cos \omega_0 t$, and the LPF 25c performs lowpass filter processing on the signal outputted from the mixer 25a, and thereby, an I-signal representing a real number component of the complex baseband signal is generated. On the other hand, the mixer 25b multiplies the reception signal, that has been converted into the digital signal by the ADC 24, by a local oscillation signal $\sin \omega_0 t$, which is obtained by shifting the phase of the local oscillation signal $\cos \omega_0 t$ by $\pi/2$, and the LPF 25d performs lowpass filter processing on the signal outputted from the mixer 25b, and thereby, a Q-signal representing an imaginary number component of the complex baseband signal is generated.

The sampling parts 26a and 26b sample (resample) the complex baseband signal (I-signal and Q-signal) generated by the orthogonal detection processing part 25. Thereby, two channels of sample data are generated. The generated two channels of sample data are stored in the memories 27a and 27b, respectively.

Here, if the baseband signal is sampled at a frequency twice the baseband frequency range, signal information is held. Accordingly, the sampling frequency of 5 MHz is enough. Thereby, compared to the case where the data is serialized while it remains as the RF signal, the sampling frequency becomes lower from 40 MHz to 5 MHz, and the volume of data becomes ⅛ and the number of samples to the depth of about 15.7 cm becomes 512. However, in order to maintain the signal information in envelope detection, phase information should be held, and thus, it is necessary to generate the complex baseband signal (I-signal and Q-signal) by orthogonal detection processing or the like, and the number of channels of data becomes twice.

Therefore, the volume of data necessary for display of one frame of image is $512 \times 64 \times 100 \times 2 \approx 6.6 \times 10^6$, and therefore, in order to display 10 frames of images per second with resolving power of 12 bits, the transmission bit rate of about 792 Mbps is necessary. Further, if the sampling frequency is set to 2.5 MHz, the number of samples to the depth of about 15.7 cm is 256 and the volume of data can be further reduced to the half, and thereby, the transmission bit rate of about 396 MHz can be obtained.

Figure 3B:
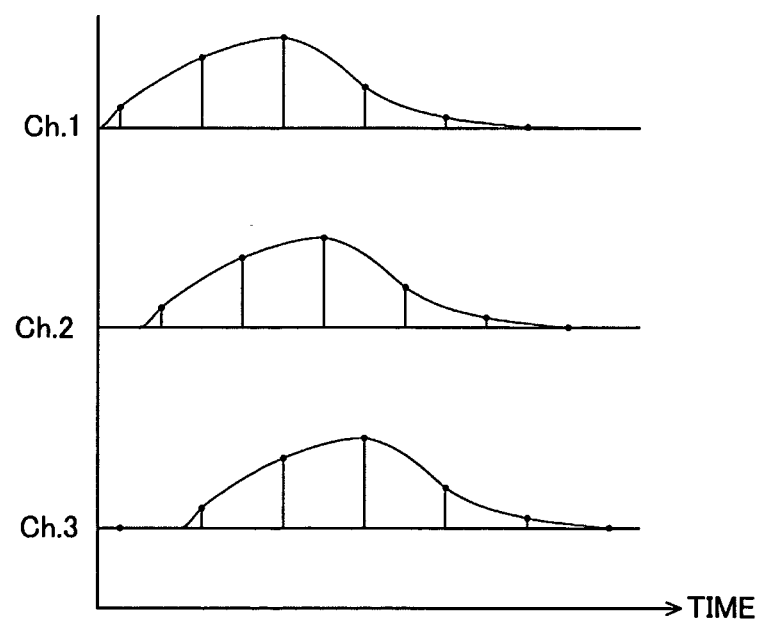
FIG. 3B is a waveform chart showing sampling by a sampling part as shown in FIG. 2.

FIGS. 3A and 3B are waveform charts respectively showing sampling by the ADC and the sampling part as shown in FIG. 2 in comparison. FIG. 3A shows sampling by the ADC 24 with respect to three channels Ch. 1 to Ch. 3, and FIG. 3B shows sampling by the sampling part 26a with respect to three channels Ch. 1 to Ch. 3. Compared to the case where the RF signals are sampled as shown in FIG. 3A and the sample data is transmitted, the transmission bit rate can be significantly reduced by sampling the baseband signals as shown in FIG. 3B and transmitting the sample data.

Figure 4:
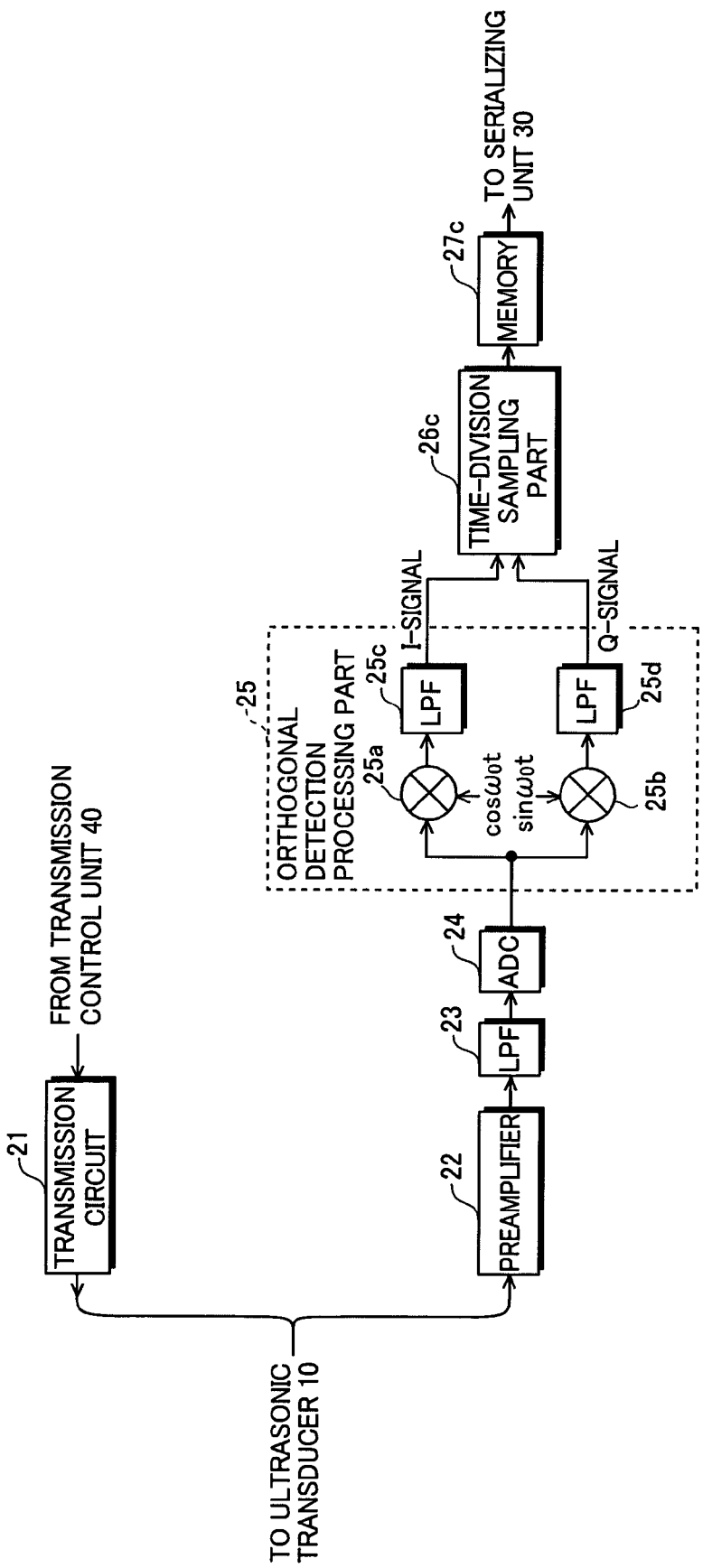
FIG. 4 shows a second configuration example of a transmitting and receiving unit as shown in FIG. 1.

FIG. 4 shows a second configuration example of the transmitting and receiving unit as shown in FIG. 1. In the second configuration example as shown in FIG. 4, a time-division sampling part 26c is provided in place of the sampling parts 26a and 26b in the first configuration example as shown in FIG. 2, and a memory part 27c is provided in place of the memories 27a and 27b.

The time-division sampling part 26c alternately and time-divisionally samples (resamples) the I-signal and Q-signal generated by the orthogonal detection processing part 25, and thereby, generates two sequences of sample data. For example, the time-division sampling part 26c samples the I-signal in synchronization with the phase of $\cos \omega_0 t$ and samples the Q-signal in synchronization with the phase of $\sin \omega_0 t$. The generated two sequences of sample data are stored in the memory 27c. Thereby, the memory circuit can be reduced in one line.

Figure 5:
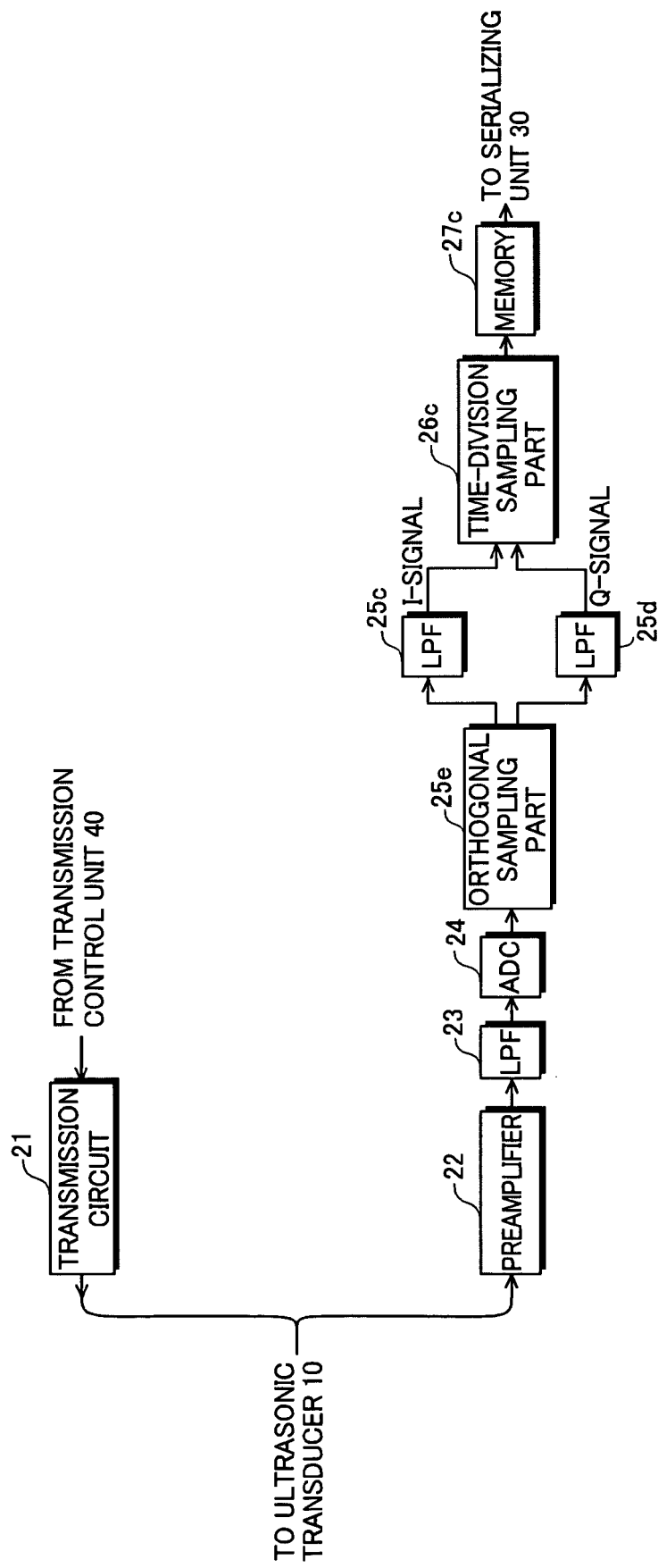
FIG. 5 shows a third configuration example of a transmitting and receiving unit as shown in FIG. 1.

FIG. 5 shows a third configuration example of the transmitting and receiving unit as shown in FIG. 1. In the third configuration example as shown in FIG. 5, an orthogonal sampling part 25e is provided in place of the mixers 25a and 25b in the second configuration example as shown in FIG. 4.

Figure 6:
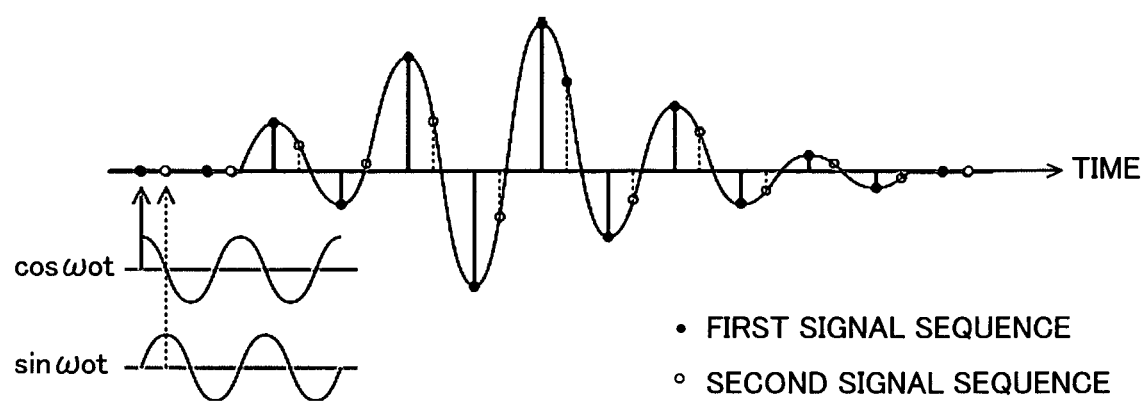
FIG. 6 is a waveform chart for explanation of an operation of an orthogonal sampling part as shown in FIG. 5.

FIG. 6 is a waveform chart for explanation of an operation of the orthogonal sampling part as shown in FIG. 5. The orthogonal sampling part 25e samples the reception signal, that has been converted into a digital signal by the ADC 24, in synchronization with the phase of $\cos \omega_0 t$ to generate a first signal sequence, and samples the reception signal in synchronization with the phase of $\sin \omega_0 t$ to generate a second signal sequence.

Further, the LPF 25c performs lowpass filter processing on the first signal sequence outputted from the orthogonal sampling part 25e to generate an I-signal representing a real number component of the complex baseband signal, and the LPF 25d performs lowpass filter processing on the second signal sequence outputted from the orthogonal sampling part 25e to generate a Q-signal representing an imaginary number component of the complex baseband signal. Thereby, the mixers 25a and 25b as shown in FIG. 4 may be omitted.

Referring to FIG. 1 again, the serializing unit 30 converts the parallel sample data generated by the plural channels of transmitting and receiving units 20 into serial sample data. For example, the serializing unit 30 converts 128 channels of parallel data obtained based on the 64 reception signals outputted from the 64 ultrasonic transducers into 1-4 channel(s) of serial sample data. Thereby, compared to the number of ultrasonic transducers 10, the number of transmission channel(s) is significantly reduced.

The transmission circuit 50 receives the scan control signal from the ultrasonic diagnostic apparatus main body 2 and outputs the received scan control signal to the transmission control unit 40, and transmits the serial sample data, that have been converted by the serializing unit 30, to the ultrasonic diagnostic apparatus main body 2. The signal transmission between the ultrasonic probe 1 and the ultrasonic diagnostic apparatus main body 2 is wiredly or wirelessly performed by using a communication method such as ASK (Amplitude Shift Keying), PSK (Phase Shift Keying), QPSK (Quadrature Phase Shift Keying), 16QAM (16 Quadrature Amplitude Modulation), for example. In the case of using ASK or PSk, one channel of serial data can be transmitted in one route, in the case of using QPSK, two channels of serial data can be transmitted in one route, and in the case of using 16QAM, four channels of serial data can be transmitted in one route.

The power supply voltage of the ultrasonic probe 1 is supplied from the ultrasonic diagnostic apparatus main body 2 when the signal transmission between the ultrasonic probe 1 and the ultrasonic diagnostic apparatus main body 2 is wiredly performed, and supplied from a battery or the like when the signal transmission between the ultrasonic probe 1 and the ultrasonic diagnostic apparatus main body 2 is wirelessly performed. When the power supply voltage of the ultrasonic probe 1 is supplied from the ultrasonic diagnostic apparatus main body 2, phantom power feed may be performed by utilizing the signal line connected between the ultrasonic probe 1 and the ultrasonic diagnostic apparatus main body 2.

In the above description, the orthogonal detection processing part 25 (FIG. 2), the sampling parts 26a and 26b (FIG. 2), the time-division sampling part 26c (FIG. 4), the orthogonal sampling part 25e (FIG. 5), the LPFs 25c and 25d (FIG. 5), and the serializing unit 30 may be formed of digital circuits such as FPGAs (Field Programmable Gate Arrays) or the like, or formed of a central processing unit (CPU) and software (programs) for allowing the CPU to perform various kinds of processing.

In the case of using the FPGAs as general-purpose circuits, even when the circuit scale is reduced, the number of mounted electronic components is little affected. However, when the circuit scale becomes smaller, the capacity of the FPGA may become smaller, and the smaller electronic components can be used, which has a great influence on the mounting area. Alternatively, the orthogonal detection processing part 25 may be formed of an analog circuit, and thereby, the ADC 24 may be omitted. In this case, A/D conversion of the complex baseband signal is performed by the sampling parts 26a and 26b or the time-division sampling part 26c.

On the other hand, the ultrasonic diagnostic apparatus main body 2 as shown in FIG. 1 has a transmission circuit 60, a scan control unit 70, a reception focusing processing unit 80, a B-mode image signal generating unit 90, a display unit 100, an operation unit 110, a control unit 120, and a storage unit 130.

The scan control unit 70 sequentially sets the transmission directions of ultrasonic beams to generate the scan control signal. The transmission circuit 60 transmits the scan control signal generated by the scan control unit 70 to the ultrasonic probe 1, and receives serial sample data from the ultrasonic probe 1. The scan control unit 70 sequentially sets the reception directions of ultrasonic echoes, and controls the reception focusing processing unit 80.

The reception focusing processing unit 80 performs reception focusing processing on the sample data received from the ultrasonic probe 1, and thereby, generates a sound ray signal along a reception direction of ultrasonic waves. The reception focusing processing unit 80 includes a memory 81 and a phase-matching and adding unit 82. The memory 81 sequentially stores serial sample data received from the ultrasonic probe 1. The phase-matching and adding unit 82 selects one reception delay pattern from among the plural reception delay patterns according to the reception direction set in the scan control unit 70, and performs reception focusing processing by providing delays to the complex baseband signals represented by the sample data based on the selected reception delay pattern, and adding the complex baseband signals to one another. By the reception focusing processing, a baseband signal (sound ray signal), in which the focus of the ultrasonic echoes is narrowed, is formed.

The B-mode image signal generating unit 90 generates a B-mode image signal as tomographic image information on tissues within the object based on the sound ray signal formed by the reception focusing processing unit 80. The B-mode image signal generating unit 90 includes an STC (sensitivity time control) unit 91, and a DSC (digital scan converter) 92. The STC unit 91 performs correction of attenuation by distance on the sound ray signal formed by the reception focusing processing unit 80 according to the depths of the reflection positions of ultrasonic waves. The DSC 92 converts (raster-converts) the sound ray signal corrected by the STC unit 91 into an image signal that follows the normal scan system of television signals and performs necessary image processing such as gradation processing so as to generate the B-mode image signal. The display unit 100 includes a display device such as an LCD, and displays an ultrasonic diagnostic image based on the B-mode image signal generated by the B-mode image signal generating unit 90.

The control unit 102 controls the scan control unit 70 and so on according to the operation of an operator using the operation unit 110. In the embodiment, the scan control unit 70, the phase-matching and adding unit 82, the B-mode image signal generating unit 90, and the control unit 120 are formed of a CPU and software (programs) for allowing the CPU to perform various kinds of processing. However, they may be formed of digital circuits or analog circuits. The software (programs) is stored in the storage unit 130. As a recording medium in the storage unit 130, not only a built-in hard disk but also a flexible disk, MO, MT, RAM, CD-ROM, DVD-ROM, or the like may be used.

Figure 7:
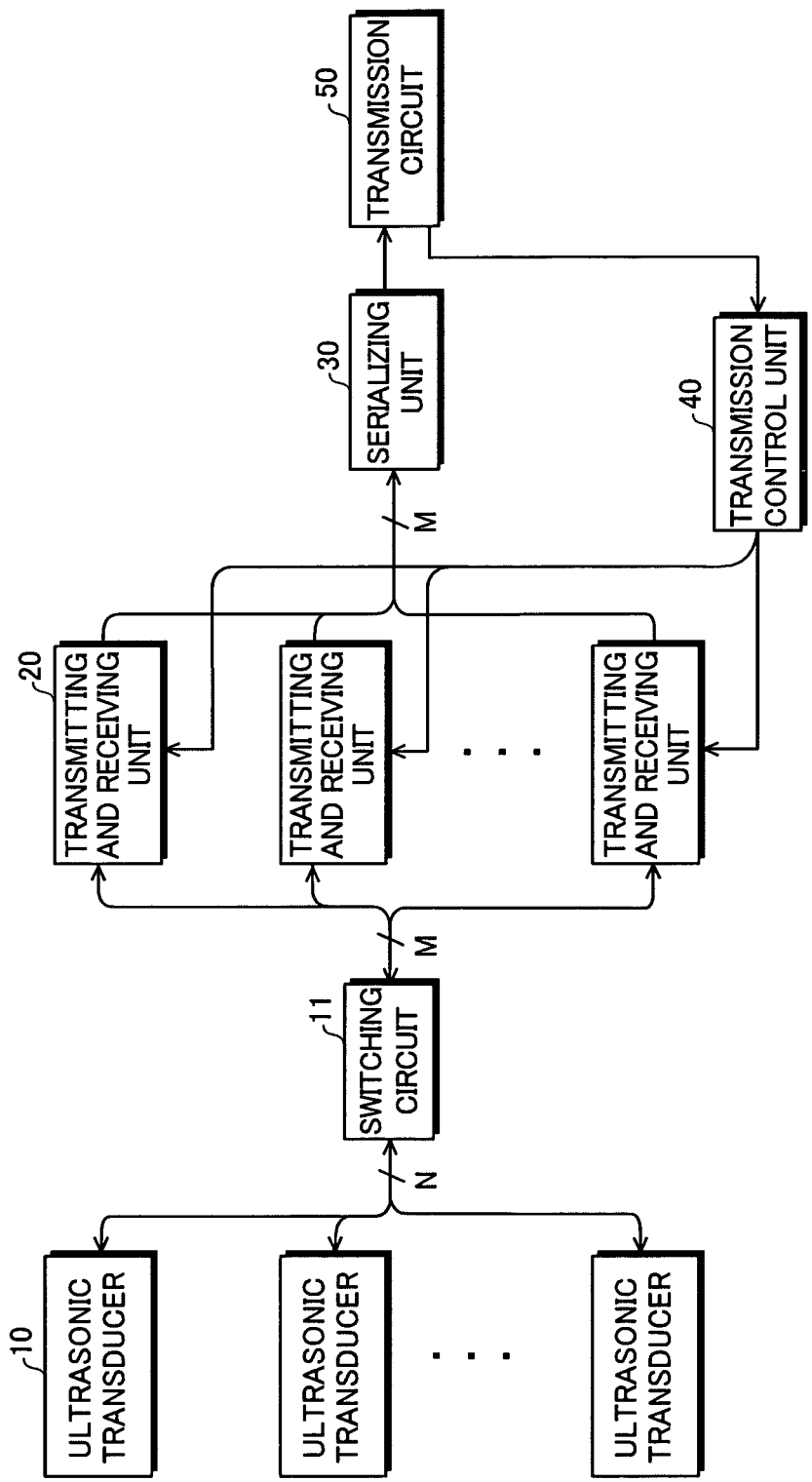
FIG. 7 is a block diagram showing a configuration of an ultrasonic probe according to a first modified example of the first embodiment of the present invention.

FIG. 7 is a block diagram showing a configuration of an ultrasonic probe according to a first modified example of the first embodiment of the present invention. In the ultrasonic probe 1' as shown in FIG. 7, a switching circuit 11 for switching the connection between the plural ultrasonic transducers 10 provided in the ultrasonic probe and the transmitting and receiving units 20 is added to the ultrasonic probe 1 as shown in FIG. 1.

Generally, in the ultrasonic probe of a linear-scan type or a convex-scan type, the object is scanned while transmission aperture and reception aperture are sequentially changed. Given that the number of ultrasonic transducers provided in the ultrasonic probe 1' is "N" and the number of ultrasonic transducers to be used at the same time is "M" (M<N), the switching circuit 11 selects M ultrasonic transducers from among the N ultrasonic transducers and connects the selected M ultrasonic transducers to the M transmitting and receiving units 20, respectively. Thereby, the number of transmitting and receiving units 20 can be reduced compared to the ultrasonic probe 1 as shown in FIG. 1.

Figure 8:
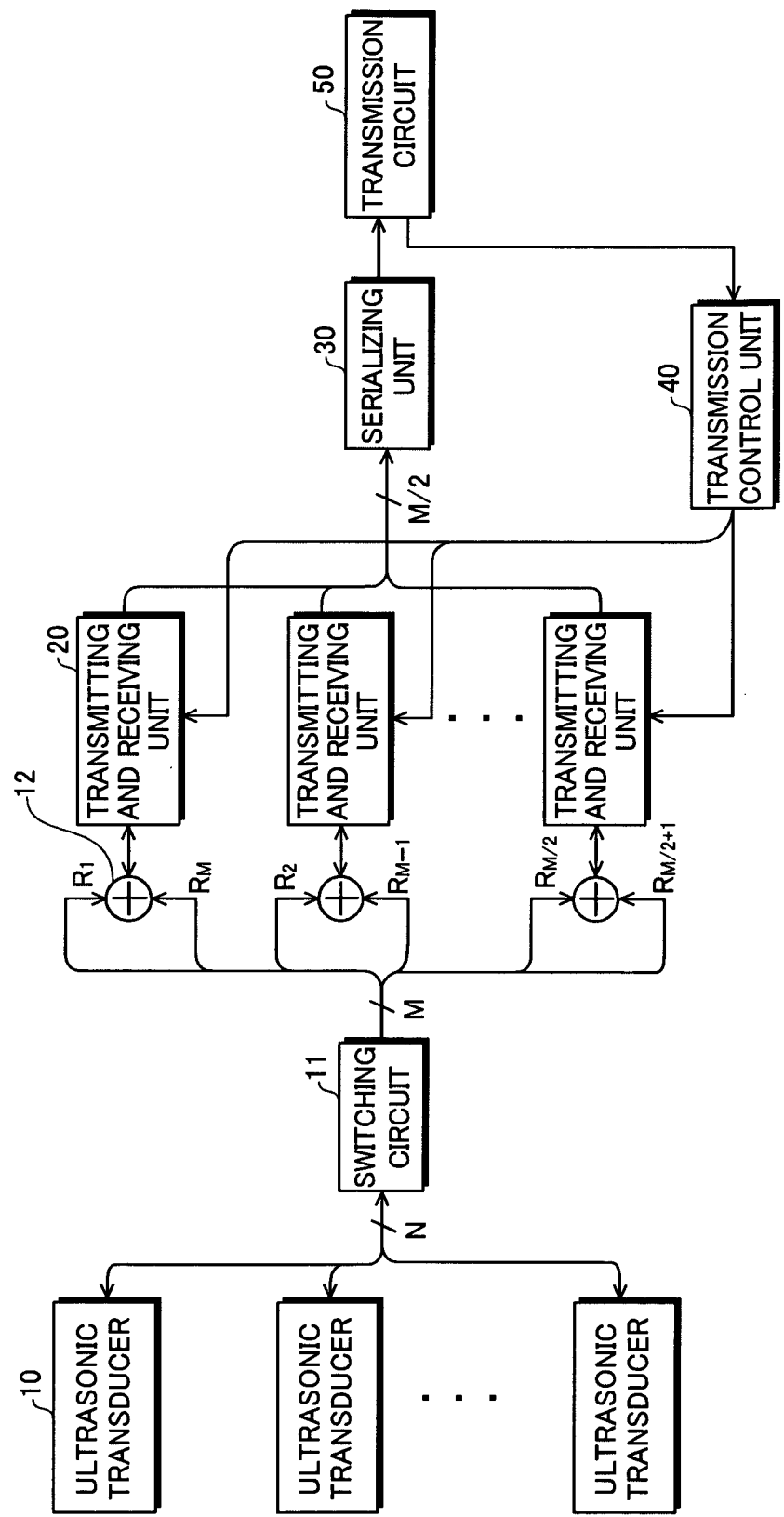
FIG. 8 is a block diagram showing a configuration of an ultrasonic probe according to a second modified example of the first embodiment of the present invention.

FIG. 8 is a block diagram showing a configuration of an ultrasonic probe according to a second modified example of the first embodiment of the present invention. In the ultrasonic probe 1" as shown in FIG. 8, addition circuits 12 for adding the reception signals outputted from the two ultrasonic transducers 10 at reception of ultrasonic waves are added to the ultrasonic probe 1' as shown in FIG. 7. At the transmission of ultrasonic waves, the addition circuits 12 supply the drive signals supplied from the transmitting and receiving units 20 to the two ultrasonic transducers 10 in parallel.

Generally, in the ultrasonic probe of a linear-scan type or a convex-scan type, the transmission and reception directions are perpendicular to the arrangement surface of the ultrasonic transducers, and thus, the amounts of delay in transmission and reception are symmetric with respect to the ultrasonic beam. Therefore, in the transmission and reception aperture formed by the M ultrasonic transducers, the amounts of delay are equal between the first ultrasonic transducer and the M-th ultrasonic transducer, and the reception signal $R_1$ and the reception signal $R_M$ may be added. Similarly, since the amounts of delay are equal between the second ultrasonic transducer and the (M−1)th ultrasonic transducer, and the reception signal $R_2$ and the reception signal $R_{M-1}$ may be added. Thereby, the number of transmitting and receiving units 20 can be reduced to the half compared to that of the ultrasonic probe 1' as shown in FIG. 7, and further, the transmission bit rate between the ultrasonic probe 1" and the ultrasonic diagnostic apparatus main body 2 can be reduced to the half.

Next, the second embodiment of the present invention will be explained. In the second embodiment, an ultrasonic probe samples an amplitude signal representing amplitude of the complex baseband signal and a phase signal representing phase of the complex baseband signal in place of the I-signal and Q-signal forming the complex baseband signal, and thereby, generates sample data. Therefore, an ultrasonic diagnostic apparatus main body generates the B-mode image signal based on the amplitude signal and the phase signal in place of the I-signal and Q-signal. The rest of the configuration is the same as that of the first embodiment.

Figure 9:
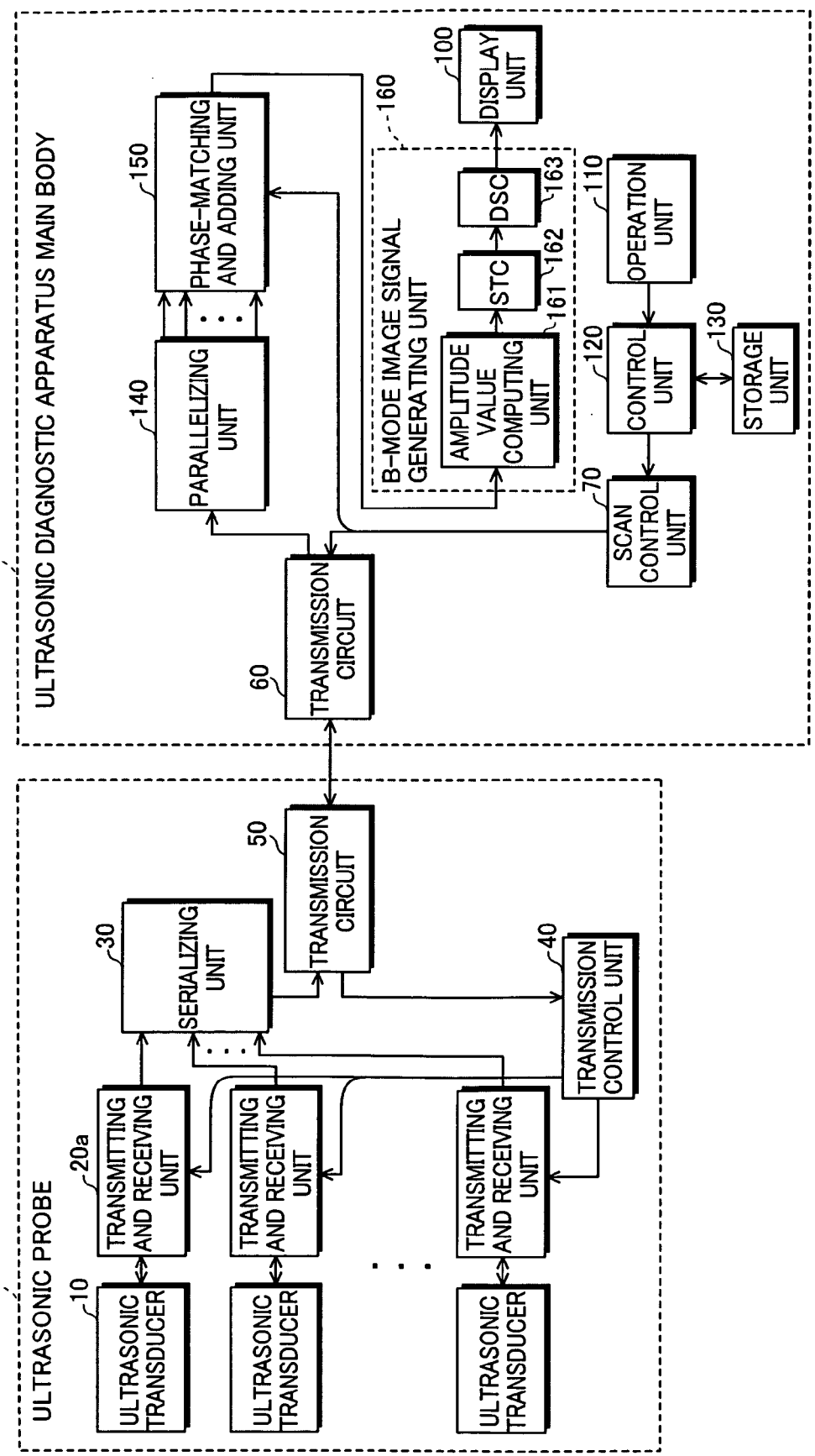
FIG. 9 is a block diagram showing a configuration of an ultrasonic diagnostic apparatus according to the second embodiment of the present invention.

FIG. 9 is a block diagram showing a configuration of an ultrasonic diagnostic apparatus according to the second embodiment of the present invention. As shown in FIG. 9, the ultrasonic diagnostic apparatus includes an ultrasonic probe 1a according to the second embodiment of the present invention and an ultrasonic diagnostic apparatus main body 2a.

As shown in FIG. 9, the ultrasonic probe 1a includes plural ultrasonic transducers 10 forming a one-dimensional or two-dimensional transducer array, plural channels of transmitting and receiving units 20a, a serializing unit 30, a transmission control unit 40, and a transmission circuit 50.

Each channel of transmitting and receiving unit 20a generates a drive signal under the control of the transmission control unit 40 and supplies the drive signal to the ultrasonic transducer 10, performs orthogonal detection processing or the like on reception signal outputted from the ultrasonic transducer 10 to generate a complex baseband signal, further generates an amplitude signal representing the amplitude of the complex baseband signal and a phase signal representing the phase of the complex baseband signal, and supplies parallel sample data generated by sampling the amplitude signal and the phase signal to the serializing unit 30.

Figure 10:
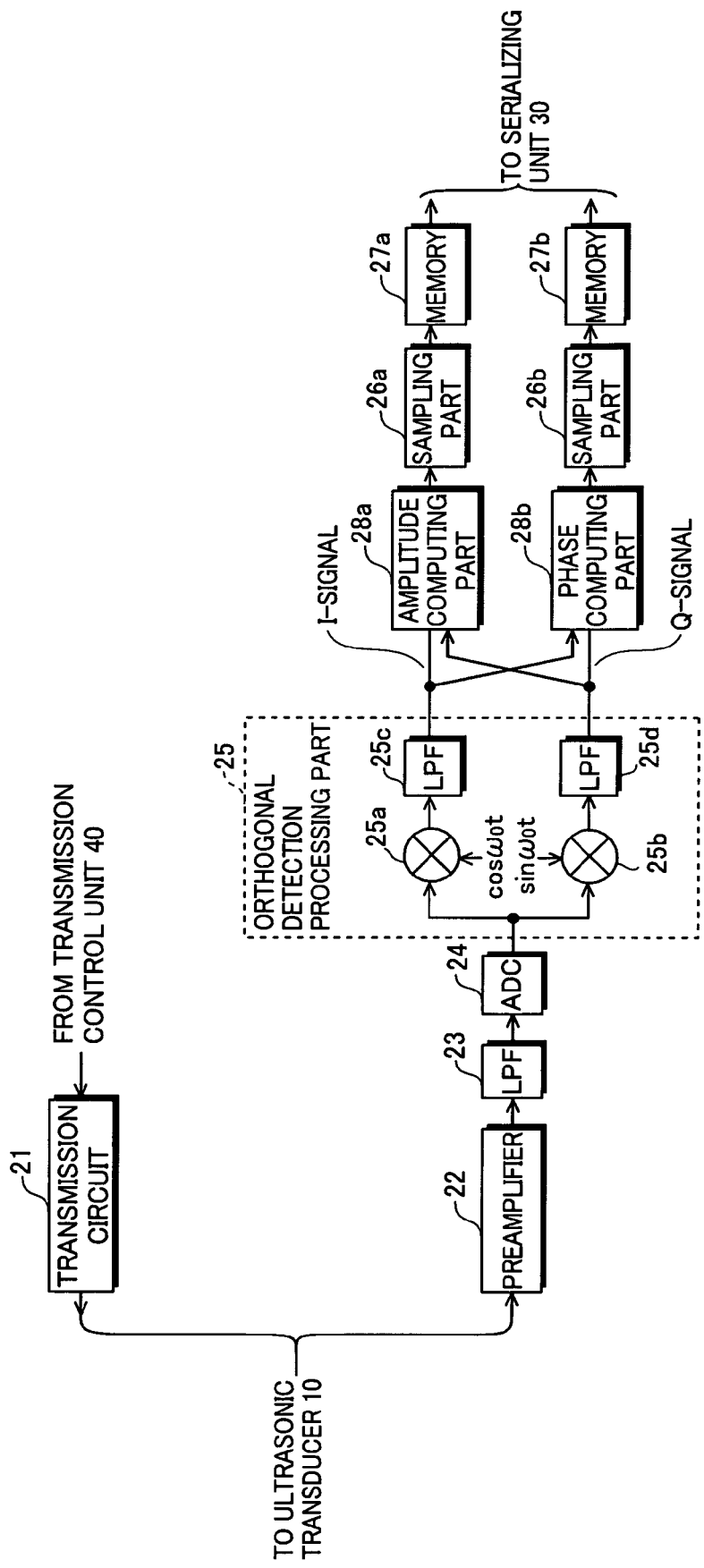
FIG. 10 shows a first configuration example of a transmitting and receiving unit as shown in FIG. 9.

FIG. 10 shows a first configuration example of the transmitting and receiving unit as shown in FIG. 9. As shown in FIG. 10, each channel of transmitting and receiving unit 20a includes a transmission circuit 21, a preamplifier 22, a low-pass filter (LPF) 23, an analog/digital converter (ADC) 24, an orthogonal detection processing part 25, an amplitude computing part 28a, a phase computing part 28b, sampling parts 26a and 26b, and memories 27a and 27b. Here, the transmission circuit 21 to the phase computing part 28b form signal processing means.

The orthogonal detection processing part 25 performs orthogonal detection processing on the reception signal to generate a complex baseband signal (I-signal and Q-signal). As shown in FIG. 10, the orthogonal detection processing part 25 includes mixers (multiplication circuits) 25a and 25b and lowpass filters (LPFs) 25c and 25d. The mixer 25a multiplies the reception signal, that has been converted into the digital signal by the ADC 24, by a local oscillation signal $\cos \omega_0 t$, and the LPF 25c performs lowpass filter processing on the signal outputted from the mixer 25a, and thereby, an I-signal representing a real number component of the complex baseband signal is generated. On the other hand, the mixer 25b multiplies the reception signal, that has been converted into the digital signal by the ADC 24, by a local oscillation signal $\sin \omega_0 t$, which is obtained by shifting the phase of the local oscillation signal $\cos \omega_0 t$ by $\pi/2$, and the LPF 25d performs lowpass filter processing on the signal outputted from the mixer 25b, and thereby, a Q-signal representing an imaginary number component of the complex baseband signal is generated.

The amplitude computing part 28a generates an amplitude signal representing the amplitude of the complex baseband signal generated by the orthogonal detection processing part 25. Here, given that the I-signal and the Q-signal forming the complex baseband signal obtained based on the reception signal outputted from the i-th ultrasonic transducer is R(i) and I(i), respectively, amplitude A(i) of the complex baseband signal is expressed by the following equation (1).

$$A(i)=(R(i)^2+I(i)^2)^{1/2} \qquad (1)$$

Further, the phase computing part 28b generates a phase signal representing the phase of the complex baseband signal generated by the orthogonal detection processing part 25. Here, given that the I-signal and the Q-signal forming the complex baseband signal obtained based on the reception signal outputted from the i-th ultrasonic transducer are R(i) and I(i), respectively, phase φ(i) of the complex baseband signal is expressed by the following equation (2).

$$\phi(i) = \arctan(I(i)/R(i)) \quad (2)$$

In the case of a 12-bit AD converter that is most widely used at present, it is appropriate that the computation word length after orthogonal detection is set to 12 bits. Therefore, if the I-signal and the Q-signal are serialized, the volume of data of 24 bits is necessary in total. On the other hand, the volume of data of the amplitude signal is $2^{1/2}$-times the volume of the I-signal or the Q-signal according to the equation (1), and 13 bits may be sufficient.

The volume of data of phase information depends on the resolving power with which the phase information within $2\pi$ is to be acquired. Since the resolving power of the phase information corresponds to time resolving power, compared to the conventional phase-matching and addition, about 1/16 of the cycle of ultrasonic waves to be transmitted may be sufficient. If so, the data length of the phase information of 4 bits is sufficient. Assuming that the data length of the phase information is 6 bits, phase control can be performed with accuracy four times compared to typical phase-matching and addition.

Even in this case, the data length of the amplitude signal and the data length of the phase signal are 19 bits in total, and therefore, the volume of data can be reduced compared to the case where the I-signal and the Q-signal are serialized. In serialization of data using amplitude information and phase information, appropriate data word lengths can be respectively selected according to the performance or scale of electronic equipment as a target.

The sampling part 26a samples (resamples) the amplitude signal generated by the amplitude computing part 28a. Further, the sampling part 26b samples (resamples) the phase signal generated by the phase computing part 28b. Thereby, two channels of sample data are generated. The generated two channels of sample data are stored in the memories 27a and 27b, respectively.

Figure 11:
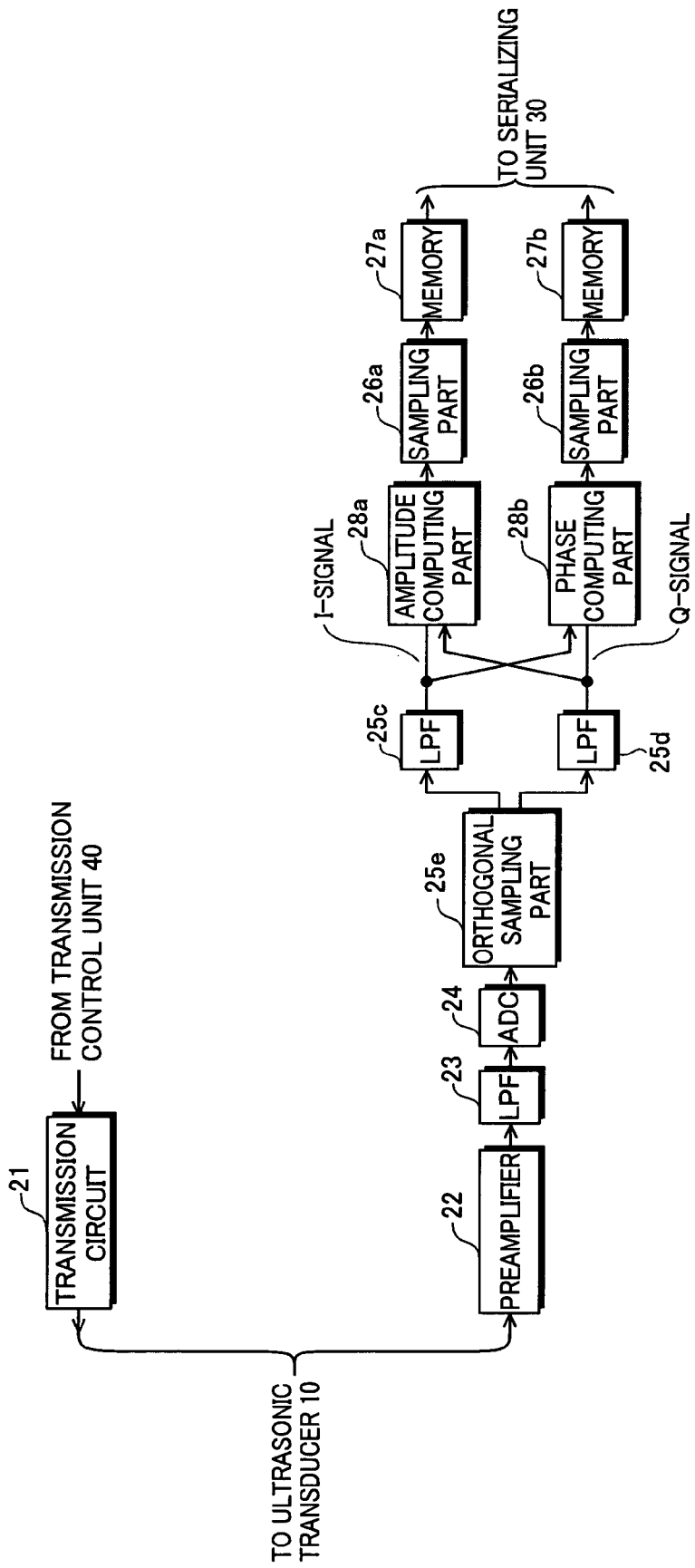
FIG. 11 shows a second configuration example of a transmitting and receiving unit as shown in FIG. 9.

FIG. 11 shows a second configuration example of the transmitting and receiving unit as shown in FIG. 9. In the second configuration example as shown in FIG. 11, an orthogonal sampling part 25e is provided in place of the mixers 25a and 25b in the first configuration example as shown in FIG. 10.

The orthogonal sampling part 25e samples the reception signal, that has been converted into a digital signal by the ADC 24, in synchronization with the phase of $\cos \omega_0 t$ to generate a first signal sequence, and samples the reception signal in synchronization with the phase of $\sin \omega_0 t$ to generate a second signal sequence (see FIG. 6).

Further, the LPF 25c performs lowpass filter processing on the first signal sequence outputted from the orthogonal sampling part 25e to generate an I-signal representing a real number component of the complex baseband signal, and the LPF 25d performs lowpass filter processing on the second signal sequence outputted from the orthogonal sampling part 25e to generate a Q-signal representing an imaginary number component of the complex baseband signal. Thereby, the mixers 25a and 25b as shown in FIG. 10 may be omitted.

Referring to FIG. 9 again, the serializing unit 30 converts the parallel sample data generated by the plural channels of transmitting and receiving units 20 into serial sample data. For example, the serializing unit 30 converts 128 channels of parallel data obtained based on the 64 reception signals outputted from the 64 ultrasonic transducers into 1-4 channel(s) of serial sample data. Thereby, compared to the number of ultrasonic transducers 10, the number of transmission channel(s) is significantly reduced.

The transmission circuit 50 receives the scan control signal from the ultrasonic diagnostic apparatus main body 2a and outputs the received scan control signal to the transmission control unit 40, and transmits the serial sample data, that have been converted by the serializing unit 30, to the ultrasonic diagnostic apparatus main body 2a. The signal transmission between the ultrasonic probe 1 and the ultrasonic diagnostic apparatus main body 2a is wiredly or wirelessly performed by using a communication method such as ASK (Amplitude Shift Keying), PSK (Phase Shift Keying), QPSK (Quadrature Phase Shift Keying), 16QAM (16 Quadrature Amplitude Modulation), for example. In the case of using ASK or PSk, one channel of serial data can be transmitted in one route, in the case of using QPSK, two channels of serial data can be transmitted in one route, and, in the case of using 16QAM, four channels of serial data can be transmitted in one route.

In the above description, the orthogonal detection processing part 25 (FIG. 10), the amplitude computing part 28a (FIG. 10), the phase computing part 28b (FIG. 10), the sampling parts 26a and 26b (FIG. 10), the orthogonal sampling part 25e (FIG. 11), the LPFs 25c and 25d (FIG. 11), and the serializing unit 30 may be formed of digital circuits, or formed of a central processing unit (CPU) and software (programs) for allowing the CPU to perform various kinds of processing. Alternatively, the orthogonal detection processing part 25 may be formed of an analog circuit, and thereby, the ADC 24 may be omitted. In this case, A/D conversion of the complex baseband signal is performed by the sampling parts 26a and 26b.

On the other hand, the ultrasonic diagnostic apparatus main body 2a as shown in FIG. 9 has a transmission circuit 60, a scan control unit 70, a parallelizing unit 140, a phase-matching and adding unit 150, a B-mode image signal generating unit 160, a display unit 100, an operation unit 110, a control unit 120, and a storage unit 130.

The scan control unit 70 sequentially sets the transmission directions of ultrasonic beams and generates the scan control signal. The transmission circuit 60 transmits the scan control signal generated by the scan control unit 70 to the ultrasonic probe 1a, and receives serial sample data from the ultrasonic probe 1a. The parallelizing unit 140 converts the serial sample data received by the transmission circuit 60 into parallel sample data, extracts amplitude signals and phase signals obtained based on the reception signals outputted from the plural ultrasonic transducers 10 from the parallel sample data, and supplies them to the phase-matching and adding unit 150. The scan control unit 70 sequentially sets the reception directions of ultrasonic echoes and controls the phase-matching and adding unit 150.

Figure 12:
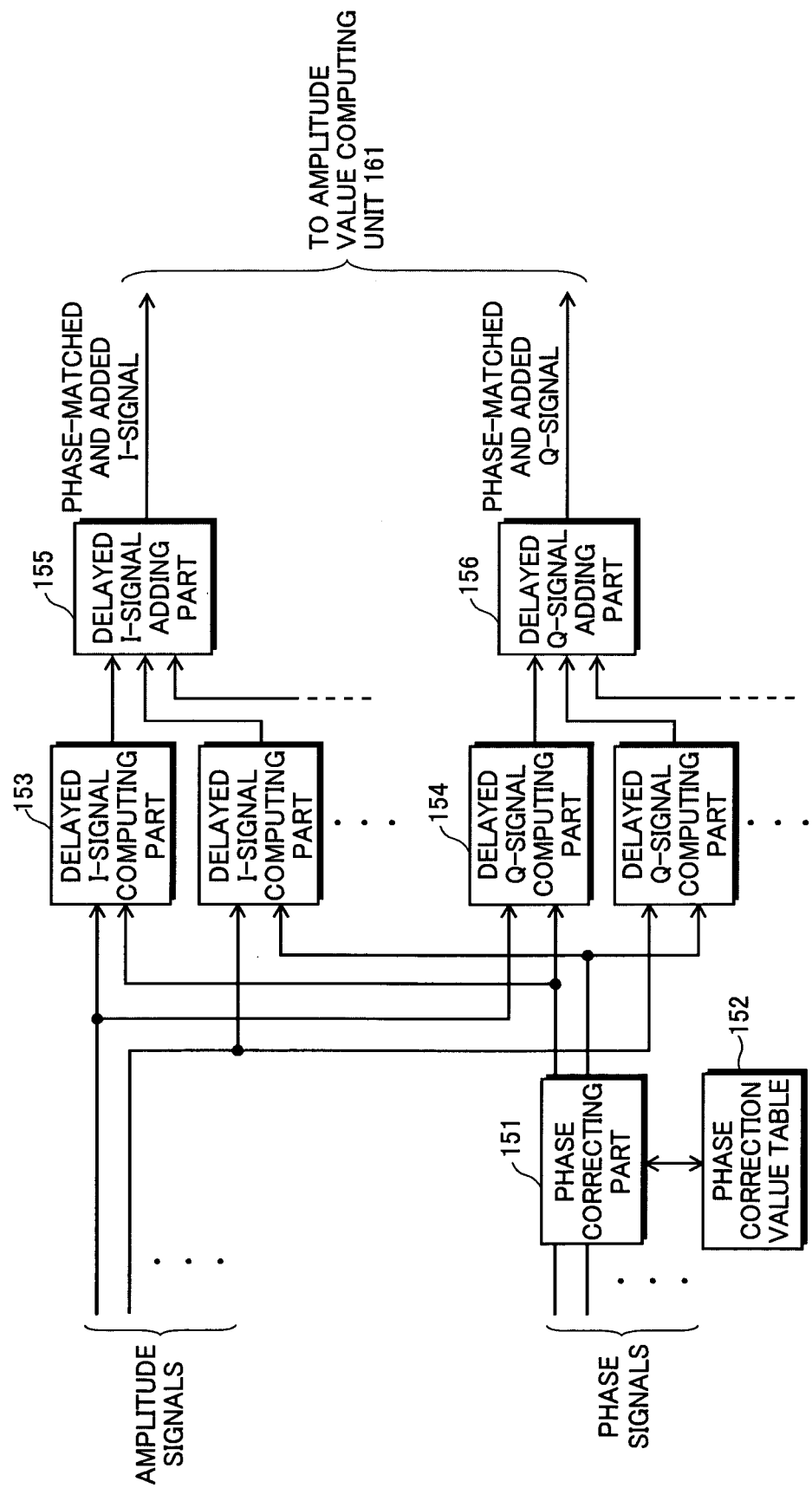
FIG. 12 shows a configuration example of a phase-matching and adding unit as shown in FIG. 9.

FIG. 12 shows a configuration example of the phase-matching and adding unit as shown in FIG. 9. As shown in FIG. 12, the phase-matching and adding unit 150 includes a phase correcting part 151, a phase correction value table 152, plural channels of delayed I-signal computing parts 153, plural channels of delayed Q-signal computing parts 154, a delayed I-signal adding part 155, and a delayed Q-signal adding part 156.

The phase correcting part 151 corrects phase values represented by the phase signals extracted by the parallelizing unit 140 according to relative positions of the reception focus and plural ultrasonic transducers by using phase correction values stored in the phase correction value table 152. The delayed I-signal computing part 153 obtains the real number component of the delayed complex baseband signal, that is, a delayed I-signal, based on the amplitude value represented by the amplitude signal extracted by the parallelizing unit 140 and the phase value corrected by the phase correcting part 151. Further, the delayed Q-signal computing part 154 obtains the imaginary number component of the delayed complex baseband signal, that is, a delayed Q-signal, based on the amplitude value represented by the amplitude signal extracted by the parallelizing unit 140 and the phase value corrected by the phase correcting part 151.

The delayed I-signal adding part 155 adds the delayed I-signals respectively obtained with respect to the plural ultrasonic transducers by the plural channels of delayed I-signal computing parts 153 to one another, and thereby, generates a phase-matched and added real number signal (phase-matched and added I-signal). Further, the delayed Q-signal adding part 154 adds the delayed Q-signals respectively obtained with respect to the plural ultrasonic transducers by the plural channels of delayed Q-signal computing parts 154 to one another, and thereby, generates a phase-matched and added imaginary number signal (phase-matched and added Q-signal).

Figure 13:
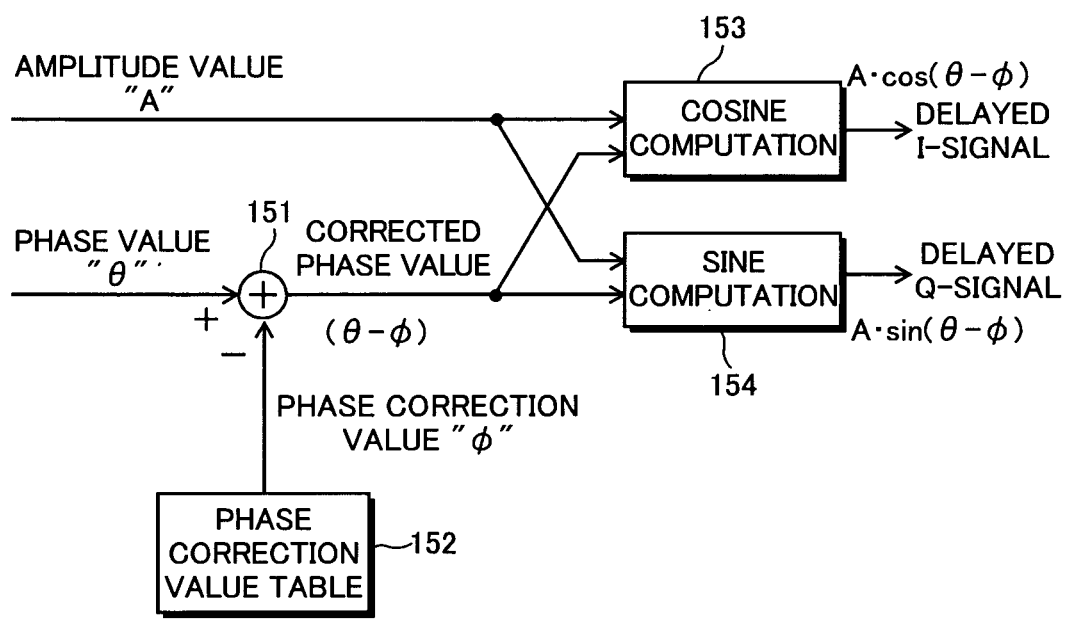
FIG. 13 is a diagram for explanation of an operation of the phase-matching and adding unit as shown in FIG. 12.

FIG. 13 is a diagram for explanation of an operation of the phase-matching and adding unit as shown in FIG. 12. FIG. 13 shows the signal processing for one channel corresponding to one ultrasonic transducer.

The phase correction value table 152 stores phase correction values $\phi$ for correction of the phase values $\theta$ represented by the phase signals, according to the geometric relative positions of the reception focus and the plural ultrasonic transducers. The phase correcting part 151 reads out the phase correction value $\phi$ from the phase correction value table 152 according to the reception direction set by the scan control unit 70, subtracts the phase correction value $\phi$ from the phase value $\theta$ represented by the phase signal, and thereby, obtains a corrected phase value $(\theta-\phi)$. This corresponds to delaying the complex baseband signal by the time period corresponding to the phase correction value $\phi$.

The delayed I-signal computing part 153 obtains $A \cdot \cos(\theta-\phi)$ as the real number component of the delayed complex baseband signal, that is, the delayed I-signal, based on the amplitude value "A" represented by the amplitude signal and the phase value $(\theta-\phi)$ corrected by the phase correcting part 151. Further, the delayed Q-signal computing part 154 obtains $A \cdot \sin(\theta-\phi)$ as the imaginary number component of the delayed complex baseband signal, that is, the delayed Q-signal, based on the amplitude value "A" represented by the amplitude signal and the phase value $(\theta-\phi)$ corrected by the phase correcting part 151.

Referring to FIG. 12 again, the delayed I-signal adding part 155 adds the delayed I-signals respectively obtained with respect to the plural ultrasonic transducers by the plural channels of delayed I-signal computing parts 153 to one another so as to perform reception focusing processing. By the reception focusing processing, a phase-matched and added I-signal with the narrowed focus of ultrasonic echoes is generated. Further, the delayed Q-signal adding part 156 adds the delayed Q-signals respectively obtained with respect to the plural ultrasonic transducers by the plural channels of delayed Q-signal computing parts 154 to one another so as to perform reception focusing processing. By the reception focusing processing, a phase-matched and added Q-signal with the narrowed focus of ultrasonic echoes is generated.

In this way, by correcting the phase value $\theta$, reception focusing processing of performing phase-matching and addition with high accuracy by using more continuous delay amount than that in the conventional case can be realized without performing data interpolation processing on the complex baseband signals obtained by orthogonal detection or the like. Further, the phase-matching and adding circuit can be simplified and the focus can be set at the higher degree of freedom.

Referring to FIG. 9 again, the B-mode image signal generating unit 160 generates a B-mode image signal representing an ultrasonic diagnostic image based on the phase-matched and added I-signal generated by the delayed I-signal adding part 155 and/or the phase-matched and added Q-signal generated by the delayed Q-signal adding part 156. Here, the B-mode refers to a mode for displaying a two-dimensional tomographic image by converting the amplitude of ultrasonic echoes into brightness. The B-mode image signal generating unit 160 includes an amplitude value computing unit 161, an STC (sensitivity time control) unit 162, and a DSC (digital scan converter) 163.

The amplitude value computing unit 161 generates a phase-matched and added signal representing an amplitude value of the phase-matched and added complex baseband signal by obtaining a square root of a sum of a square of the phase-matched and added I-signal and a square of the phase-matched and added Q-signal. The STC unit 162 performs correction of attenuation by distance according to the depth of the reflection position of ultrasonic waves on the phase-matched and added signal generated by the phase-matching and adding unit 150.

The DSC 163 converts (raster-converts) the phase-matched and added signal corrected by the STC unit 162 into an image signal that follows the normal scan system of television signals and performs necessary image processing such as gradation processing to generate a B-mode image signal. The display unit 100 includes a display device such as an LCD, and displays an ultrasonic diagnostic image based on the B-mode image signal generated by the B-mode image signal generating unit 160.

Alternatively, the B-mode image signal generating unit 160 can generate an image signal based on one of the phase-matched and added I-signal and the phase-matched and added Q-signal. In this case, the amplitude value computing unit 161 may be omitted, and the delayed Q-signal computing part 154 and the delayed Q-signal adding part 156 may be omitted, or the delayed I-signal computing part 153 and the delayed I-signal adding part 155 may be omitted.

The control unit 120 controls the scan control unit 70 and so on according to the operation of an operator using the operation unit 110. In the embodiment, the scan control unit 70, the parallelizing unit 140, the phase-matching and adding unit 150, the B-mode image signal generating unit 160, and the control unit 120 are formed of a CPU and software (programs) for allowing the CPU to perform various kinds of processing. However, they may be formed of digital circuits or analog circuits. The software (programs) is stored in the storage unit 130. As a recording medium in the storage unit 130, not only a built-in hard disk but also a flexible disk, MO, MT, RAM, CD-ROM, DVD-ROM, or the like may be used.

Here, a principle of the present invention will be explained in detail by referring to FIGS. 14 and 15.

Figure 14:
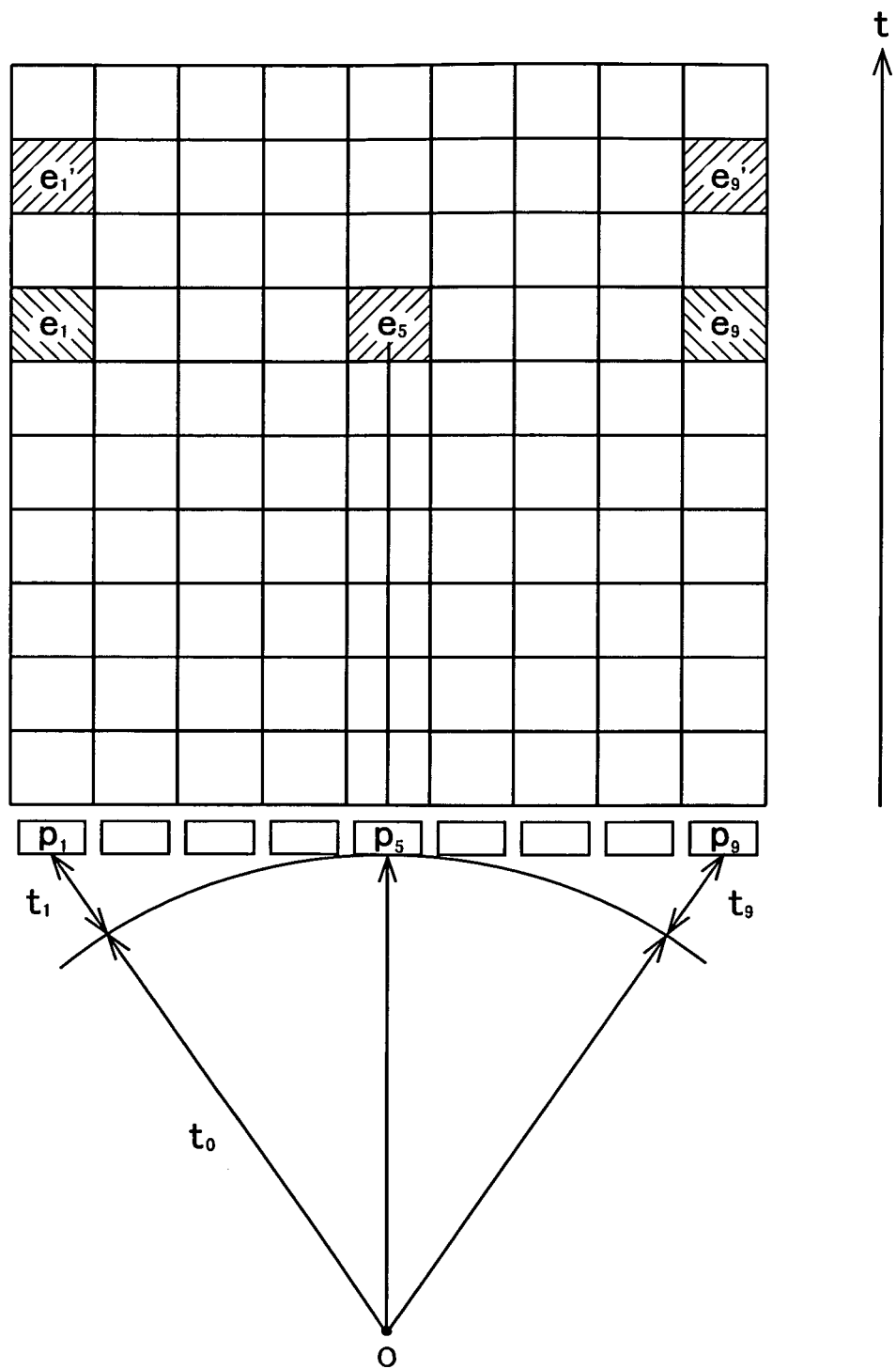
FIG. 14 shows a state of reception signals when an ultrasonic beam is transmitted toward a direction of point "O" by arranged vibrators.
Figure 15:
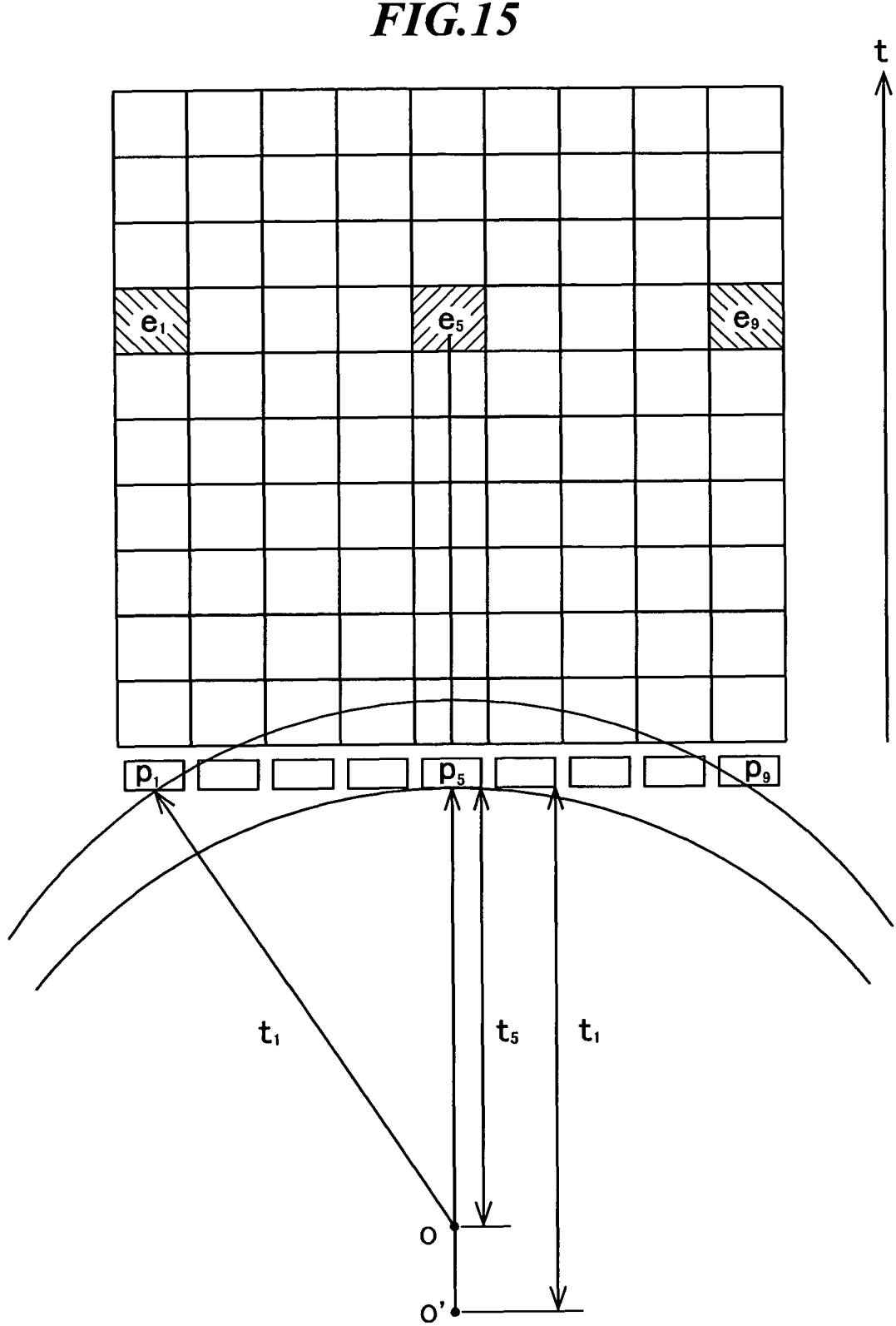
FIG. 15 shows a state of reception signals when an ultrasonic beam is transmitted toward the direction of point "O" by the arranged vibrators.

FIGS. 14 and 15 show states of reception signals when an ultrasonic beam is transmitted toward a direction of point "O" by arranged vibrators. In FIG. 14, a matrix above vibrators $p_1$-$p_9$ represents digitized reception signals. The columns above the respective vibrators indicate reception signals from the vibrators at time "t". For example, when the vibrator $p_5$ at the center receives ultrasonic echoes from point "O" at a certain time, the reception signal is stored in a location of $e_5$. The reception signals from the vibrators $p_1$ and $p_9$ at ends received at the same timing are stored in locations of $e_1$ and $e_9$.

However, those reception signals represent ultrasonic echoes from distances nearer than the point "O", and the ultrasonic echoes from the point "O" reach with delays of times $t_1$ and $t_9$, respectively. In FIG. 14, the echoes are stored in locations of $e_1'$ and $e_9'$, respectively. If the point "O" is immediately below the vibrator $p_5$, then $t_1 = t_9$, and the locations of $e_1'$ and $e_9'$ are the same in respective columns. In conventional beam forming, there is employed a method of actually delaying the reception signal in the location of $e_5$ by time $t_1$ and adding it to the reception signals in the locations of $e_1'$ and $e_9'$.

In FIG. 15, the reception signal e(nT) in the location of $e_1$ by the vibrator $p_1$ is assumed to be expressed by the equation 3.

$$e(nT) = A(nT) \cdot \exp\{j(2\pi f_0 nT + \theta_0)\} \quad (3)$$

where A(nT) is signal intensity of ultrasonic echoes from the point "O", nT is n-th data AD-converted at a sampling rate having a sampling interval "T". The reception signal has phase rotation corresponding to the time nT for transmission frequency $f_0$, and $\theta_0$ is an initial value of the phase according to depth. Here, the reception signal $e_i(nT)$ received at the same time by another vibrator is expressed by the equation (4).

$$e_i(nT) = A(nT + t(i,n)) \cdot \exp\{j(2\pi f_0(nT + t(i,n)) + \theta_0)\} \quad (4)$$

The reception signal $e_i(nT)$ is a signal from the depth corresponding to the time $t_1$, and thus, a reception signal from point "O'" deeper than the point "O". For example, in FIG. 15, in consideration of the reception signal by the vibrator $p_5$, it precedes by the time $(t_1-t_5)$ compared to the reception signal in the location of $e_1$. The time difference is defined by the location of the vibrator and the reception time, and can be expressed by t(i,n). Further, t(i,n) can be calculated from the geometric relative positions of the sound source and the vibrator. In the conventional beam forming, phase-matching and addition is performed by delaying the reception signal $e_i(nT)$ by the time difference t(i,n) so that the reception signal $e_i(nT)$ is in phase with the reception signal e(nT) and adding those signals to each other.

In the baseband method, the reception signal is orthogonally detected and converted into an I-signal and a Q-signal in the baseband of the reception signal. The reception signal expressed by the equations (3) and (4) is converted into the baseband and expressed by the equations (5) and (6).

$$E(nT) = e(nT) \cdot \exp\{-j(2\pi f_0 nT)\} \quad (5)$$
$$= A(nT) \cdot \exp\{-j\theta_0\}$$

$$E_i(nT) = e_i(nT) \cdot \exp\{-j(2\pi f_0 nT)\} \quad (6)$$
$$= A(nT + t(i,n)) \cdot \exp\{j(2\pi f_0 t(i,n) + \theta_0)\}$$

Here, if t(i,n)>nT, the sample point "n" may be changed to obtain the condition of t(i,n)<nT. For example, the replacement of $t(i,n) = mT + t_i$ is possible, and m-th data is used in place of the n-th data in $E_i(nT)$. This means using data corresponding to different depths in the memory, and here, $t_i < T$. If the time is before re-sampling, $T < 1/(2f_0)$ and $2\pi f_0 t_i < \pi$. This shows that the delays of "T" or more can be corrected by using the data at different sample points, and that correction may be performed only on the delays $t_i$ less than "T". From that, the equation (6) can be replaced by the equation (7).

$$E_i(nT) = A(mT + t_i) \cdot \exp\{j(2\pi f_0 t_i + \theta_0)\} \quad (7)$$

Here, in consideration that $t_i$ is sufficiently small, $A(mT + t_i)$ can be replaced by A(nT) because the difference is thought to be smaller than the resolving power. For simplification, replacement is performed as expressed by the equations (8) and (9). Here, An and $\theta n_i$ are an amplitude and a phase after orthogonal detection, respectively.

$$A(mT + t_i) = A(nT) = An \quad (8)$$

$$2\pi f_0 t_i + \theta_0 = \theta n_i \quad (9)$$

Accordingly, delaying the signal in the equation (7) by the time $t_i$ corresponds to turning back the phase by the amount corresponding to the time $t_i$. Therefore, the I-signal and the Q-signal can be obtained by the equations (10) and (11), respectively.

$$Rn_i = An \cdot \cos\{\theta n_i - \phi(i,n)\} \quad (10)$$

$$In_i = An \cdot \sin\{\theta n_i - \phi(i,n)\} \quad (11)$$

Here, $\phi(i,n)$ is expressed by the equation (12) and can be calculated from the geometric relative positions of the sound source and the vibrator.

$$\phi(i,n) = 2\pi f_0 t(i,n) \quad (12)$$

The I-signals and Q-signals obtained from the equations (10) and (11) in the number of vibrators are added to one another, and thereby, phase-matched and added information Rn and In can be obtained as expressed by the equations (13) and (14).

$$Rn = \sum_i Rn_i \quad (13)$$

$$In = \sum_i In_i \quad (14)$$

For image display, for example, an amplitude value Vn may be calculated as expressed by the equation (15) based on the phase-matched and added equations (13) and (14).

$$Vn = \sqrt{Rn^2 + In^2} \quad (15)$$

In the second embodiment, as is the case shown in FIG. 7, a switching circuit for switching the connection between the plural ultrasonic transducers and the transmitting and receiving units provided in the ultrasonic probe may be added. Alternatively, as shown in FIG. 8, an addition circuit for adding reception signals outputted from two ultrasonic transducers at reception of ultrasonic waves may be added.

The invention claimed is:

1. An ultrasonic probe comprising:
   plural ultrasonic transducers configured to transmit ultrasonic waves according to drive signals and receive ultrasonic echoes to output reception signals;
   signal processing parts each configured to perform one of quadrature detection processing and quadrature sampling processing on the reception signal outputted from respective one of said plural ultrasonic transducers to generate first and second signals representing a complex baseband signal and then generate an amplitude signal representing an amplitude of the complex baseband signal and a phase signal representing a phase of the complex baseband signal, a sum of a bit length of the amplitude signal and a bit length of the phase signal being less than a sum of a bit length of the first signal and a bit length of the second signal;
   sampling parts each configured to sample the amplitude signal and the phase signal generated by respective one of said signal processing parts to generate parallel sample data;

a serializing unit configured to convert the parallel sample data generated by said sampling parts into serial sample data; and a transmission circuit configured to transmit the serial sample data converted by said serializing unit.

2. The ultrasonic probe according to claim 1, wherein each of said signal processing parts includes:
- a preamplifier configured to amplify the reception signal outputted from respective one of said plural ultrasonic transducers;
- a lowpass filter configured to limit a band of the reception signal outputted from said preamplifier;
- an analog/digital converter configured to convert an analog reception signal outputted from said lowpass filter into a digital reception signal;
- a quadrature detection processing part configured to perform quadrature detection processing on the digital reception signal converted by said analog/digital converter to generate the complex baseband signal;
- an amplitude computing part configured to generate the amplitude signal representing the amplitude of the complex baseband signal generated by said quadrature detection processing part; and
- a phase computing part configured to generate the phase signal representing the phase of the complex baseband signal generated by said quadrature detection processing part.

3. The ultrasonic probe according to claim 1, wherein each of said signal processing parts includes:
- a preamplifier configured to amplify the reception signal outputted from respective one of said plural ultrasonic transducers;
- a lowpass filter configured to limit a band of the reception signal outputted from said preamplifier;
- an analog/digital converter configured to convert an analog reception signal outputted from said lowpass filter into a digital reception signal;
- an orthogonal sampling part configured to perform quadrature sampling processing on the digital reception signal converted by said analog/digital converter to generate a first signal sequence and a second signal sequence;
- lowpass filters configured to limit bands of the first and second signal sequences generated by said orthogonal sampling part to generate the complex baseband signal;
- an amplitude computing part configured to generate the amplitude signal representing the amplitude of the complex baseband signal generated by said lowpass filters; and
- a phase computing part configured to generate the phase signal representing the phase of the complex baseband signal generated by said lowpass filters.

4. The ultrasonic probe according to claim 1, further comprising:
- a switching circuit configured to switch connection between the plural ultrasonic transducers provided in said ultrasonic probe and said signal processing parts.

5. The ultrasonic probe according to claim 1, wherein said signal processing parts further include plural transmission circuits configured to respectively supply the drive signals to said plural ultrasonic transducers.

6. The ultrasonic probe according to claim 1, wherein said transmission circuit is configured to wirelessly transmit the serial sample data converted by said serializing unit.

7. An ultrasonic diagnostic apparatus comprising:
- an ultrasonic probe including plural ultrasonic transducers configured to transmit ultrasonic waves according to drive signals and receive ultrasonic echoes to output reception signals, signal processing parts each configured to perform one of quadrature detection processing and quadrature sampling processing on the reception signal outputted from respective one of said plural ultrasonic transducers to generate first and second signals representing a complex baseband signal and then generate an amplitude signal representing an amplitude of the complex baseband signal and a phase signal representing a phase of the complex baseband signal, a sum of a bit length of the amplitude signal and a bit length of the phase signal being less than a sum of a bit length of the first signal and a bit length of the second signal, sampling parts each configured to sample the amplitude signal and the phase signal generated by respective one of said signal processing parts to generate parallel sample data, a serializing unit configured to convert the parallel sample data generated by said sampling parts into serial sample data, and a transmission circuit configured to transmit the serial sample data converted by said serializing unit;
- a parallelizing unit configured to convert the serial sample data transmitted from said ultrasonic probe into parallel sample data and extract the amplitude signal and the phase signal from the parallel sample data;
- a phase correcting part configured to correct a phase value represented by the phase signal extracted by said parallelizing unit according to relative positions of a reception focus and said plural ultrasonic transducers;
- at least one of delayed I-signal computing parts and delayed Q-signal computing parts each configured to obtain a real number component or an imaginary number component of the complex baseband signal based on an amplitude value represented by the amplitude signal extracted by said parallelizing unit and the phase value corrected by said phase correcting part; and
- an adding part configured to add real number components of complex baseband signals obtained with respect to said plural ultrasonic transducers by said delayed I-signal computing parts to generate a phase-matched and added real number signal, and/or adding imaginary number components of complex baseband signals obtained with respect to said plural ultrasonic transducers by said delayed Q-signal computing parts to generate a phase-matched and added imaginary number signal.

8. The ultrasonic diagnostic apparatus according to claim 7, wherein:
- said ultrasonic diagnostic apparatus comprises said delayed I-signal computing parts each configured to obtain the real number component of the complex baseband signal, and said delayed Q-signal computing parts each configured to obtain the imaginary number component of the complex baseband signal; and
- said adding part is configured to add the real number components of the complex baseband signals obtained with respect to said plural ultrasonic transducers by said delayed I-signal computing parts to generate the phase-matched and added real number signal, and adds the imaginary number components of the complex baseband signals obtained with respect to said plural ultrasonic transducers by said delayed Q-signal computing parts to generate the phase-matched and added imaginary number signal.

9. The ultrasonic diagnostic apparatus according to claim 8, further comprising:
- a B-mode image signal generating unit configured to generate an image signal representing an ultrasonic diagnostic image based on a square root of a sum of a square of the phase-matched and added real number signal and a square of the phase-matched and added imaginary number signal obtained by said adding part.

10. The ultrasonic diagnostic apparatus according to claim 7, further comprising:
a memory containing a phase correction value table configured to store phase correction values to be used for correcting the phase value for a time difference according to relative positions of a reception focus and said plural ultrasonic transducers,
wherein said phase correcting part is configured to read out a phase correction value from said memory containing said phase correction value table according to a reception direction, and correct the phase value represented by the phase signal extracted by said parallelizing unit, by using the phase correction value.

* * * * *